US012773474B2

(12) United States Patent
Lopez et al.

(10) Patent No.: US 12,773,474 B2
(45) **Date of Patent: *Oct. 27, 2026**

(54) VASCULAR REPAIR PATCH

(71) Applicant: INSTITUT QUIMIC DE SARRIA CETS FUNDACIO PRIVADA, Barcelona (ES)

(72) Inventors: Jordi Martorell Lopez, Barcelona (ES); Salvador Borros Gomez, Barcelona (ES); Noemi Bala Palasi, Barcelona (ES); Mercedes Balcells Camps, Barcelona (ES)

(73) Assignee: INSTITUT QUIMIC DE SARRIA CETS FUNDACIO PRIVADA, Barcelona (ES)

( * ) Notice: Subject to any disclaimer, the term of this patent is extended or adjusted under 35 U.S.C. 154(b) by 69 days.

This patent is subject to a terminal disclaimer.

(21) Appl. No.: 18/589,809

(22) Filed: Feb. 28, 2024

(65) Prior Publication Data

US 2024/0197960 A1 Jun. 20, 2024

Related U.S. Application Data

(63) Continuation of application No. 16/980,247, filed as application No. PCT/EP2019/056358 on Mar. 13, 2019, now Pat. No. 11,944,723.

(30) Foreign Application Priority Data

Mar. 13, 2018 (EP) .................................... 18382165

(51) Int. Cl.
*A61F 2/06* (2013.01)
*A61F 2/00* (2006.01)
(Continued)

(52) U.S. Cl.
CPC .......... *A61L 27/507* (2013.01); *A61F 2/0095* (2013.01); *A61F 2/06* (2013.01);
(Continued)

(58) Field of Classification Search
CPC .. A61F 2/06; A61F 2220/0016; A61L 27/507; A61L 27/18; A61L 27/26;
(Continued)

(56) References Cited

U.S. PATENT DOCUMENTS

2003/0171053 A1* 9/2003 Sanders .................... B32B 5/02
442/341
2008/0220042 A1* 9/2008 Hashi ...................... A61L 27/54
514/6.9

(Continued)

OTHER PUBLICATIONS

Franco et al.; Preparation and characterization of electrospun PCL/PLGA membranes and chitosan/gelatin hydrogels for skin bioengineering applications; J Master Sci: Mater Med; 22:2207-2218 (2011) (Year: 2011).*

*Primary Examiner* — Dinah Baria
(74) *Attorney, Agent, or Firm* — McAfee & Taft

(57) ABSTRACT

A vascular repair patch comprises a polymeric substrate having first and second major surfaces, and at least first and second polymer filament layers, wherein the polymer filaments of the first polymer filament layer are oriented in parallel and the polymer filaments of the second polymer filament layer are oriented randomly. The patch may further include thrombogenic agents and/or extracellular matrix compounds to promote vascular tissue regeneration at the repair site. Further, included are methods of making and using the patch.

18 Claims, 14 Drawing Sheets

(51) Int. Cl.
*A61L 27/18* (2006.01)
*A61L 27/26* (2006.01)
*A61L 27/34* (2006.01)
*A61L 27/36* (2006.01)
*A61L 27/50* (2006.01)
*A61L 27/54* (2006.01)
*A61L 27/58* (2006.01)

(52) U.S. Cl.
CPC ............... *A61L 27/18* (2013.01); *A61L 27/26* (2013.01); *A61L 27/34* (2013.01); *A61L 27/3633* (2013.01); *A61L 27/54* (2013.01); *A61L 27/58* (2013.01); *A61F 2220/0016* (2013.01); *A61L 2300/418* (2013.01); *A61L 2420/02* (2013.01)

(58) Field of Classification Search
CPC ...... A61L 27/34; A61L 27/3633; A61L 27/54; A61L 27/58; A61L 2300/418; A61L 2420/02
See application file for complete search history.

(56) References Cited

U.S. PATENT DOCUMENTS

| | | | | |
|---|---|---|---|---|
| 2010/0233115 A1* | 9/2010 | Patel | ....................... | A61L 15/26 425/174.8 E |
| 2014/0257348 A1* | 9/2014 | Priewe | .................... | A61L 15/64 606/151 |

* cited by examiner 601
602
Blood flow
Vascular wound 603
604
Delivery system
Patch 606
605

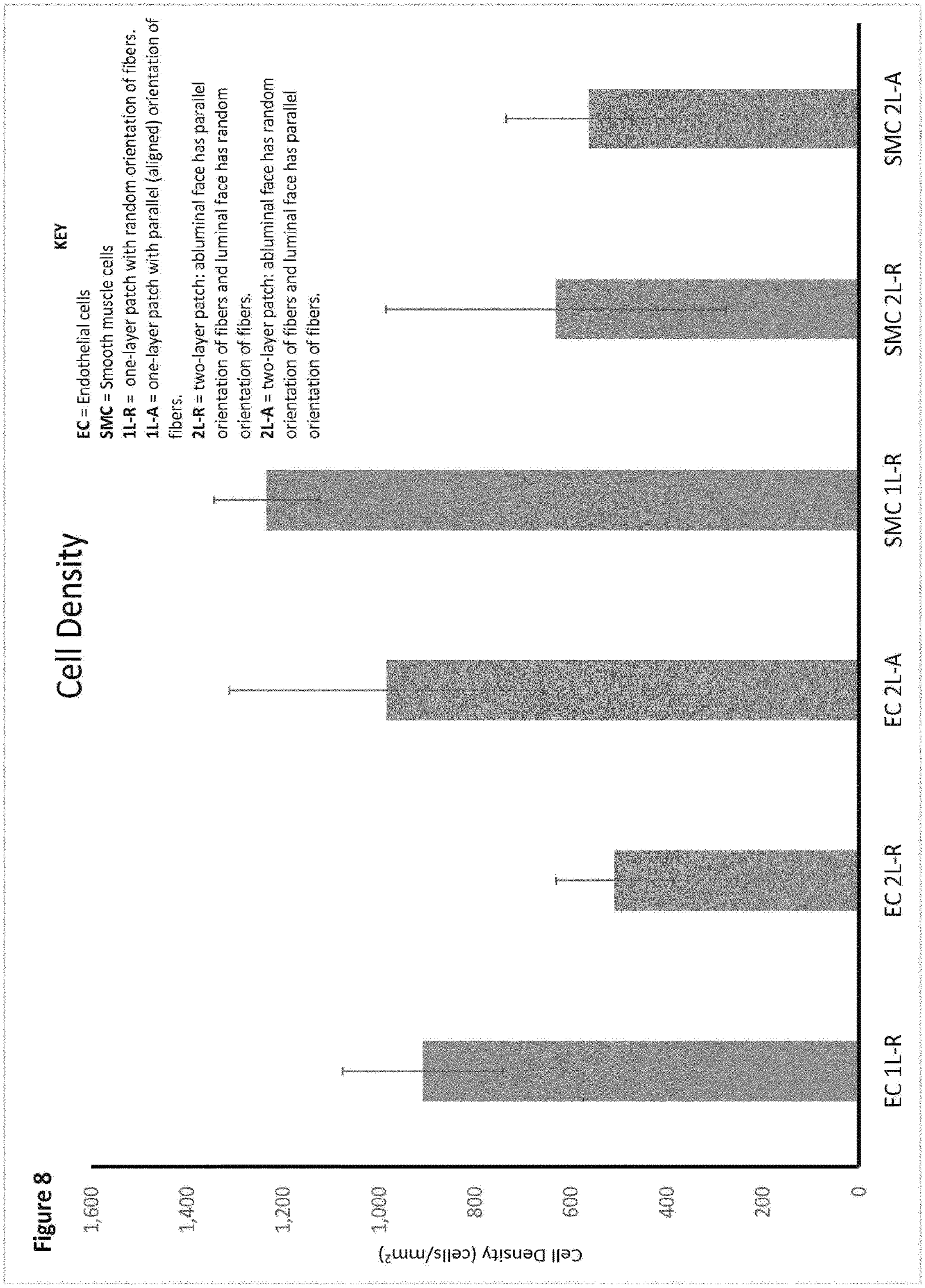
Figure 8
Cell Density
KEY
EC = Endothelial cells
SMC = Smooth muscle cells
1L-R = one-layer patch with random orientation of fibers.
1L-A = one-layer patch with parallel (aligned) orientation of fibers.
2L-R = two-layer patch: abluminal face has parallel orientation of fibers and luminal face has random orientation of fibers.
2L-A = two-layer patch: abluminal face has random orientation of fibers and luminal face has parallel orientation of fibers.
Cell Density (cells/mm²)
1,600
1,400
1,200
1,000
800
600
400
200
0
EC 1L-R
EC 2L-R
EC 2L-A
SMC 1L-R
SMC 2L-R
SMC 2L-A

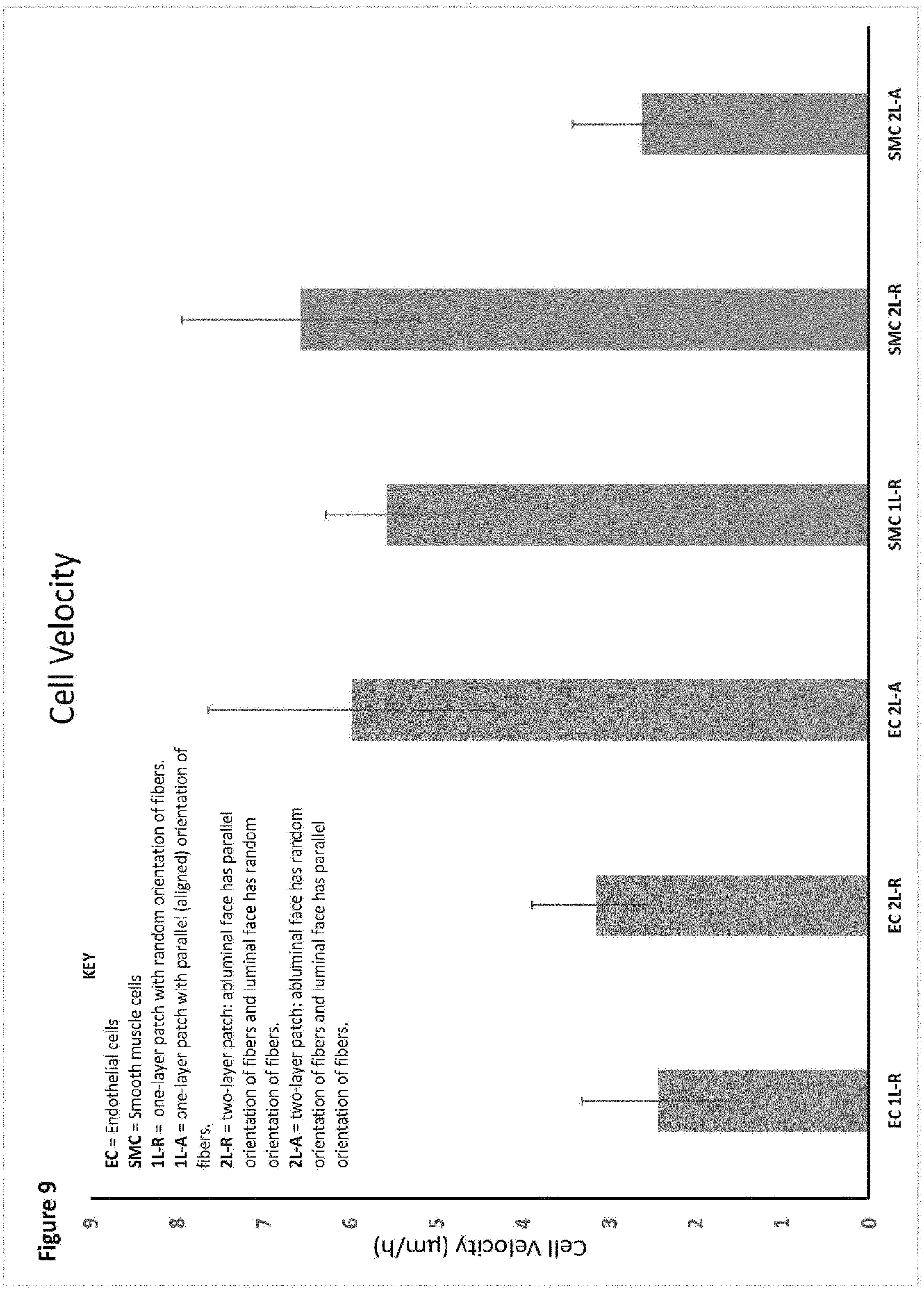
Figure 9
Cell Velocity
KEY
EC = Endothelial cells
SMC = Smooth muscle cells
1L-R = one-layer patch with random orientation of fibers.
1L-A = one-layer patch with parallel (aligned) orientation of fibers.
2L-R = two-layer patch: abluminal face has parallel orientation of fibers and luminal face has random orientation of fibers.
2L-A = two-layer patch: abluminal face has random orientation of fibers and luminal face has parallel orientation of fibers.
Cell Velocity (µm/h)
0
1
2
3
4
5
6
7
8
9
EC 1L-R
EC 2L-R
EC 2L-A
SMC 1L-R
SMC 2L-R
SMC 2L-A

VASCULAR REPAIR PATCH

CROSS REFERENCE TO RELATED APPLICATION

This Application is a continuation application of U.S. Ser. No. 16/980,257, now allowed, filed Sep. 11, 2020, which is a national stage filing of PCT/EP2019/056358, filed Mar. 13, 2019, which claims priority to EP 18382165.1 filed Mar. 13, 2018. All of which are hereby incorporated by reference.

FIELD OF THE INVENTION

This application relates to a tissue repair device that is useful for the repair of damaged vasculature. More specifically, the application relates to a device in the form of an engineered polymeric patch which adheres to a damaged blood vessel to cover and reinforce a vascular defect and which promotes vascular regeneration. The invention further relates to methods of making the device and to methods of using the device for the repair of damaged vasculature, particularly the repair of aortic dissections.

BACKGROUND TO THE INVENTION

Blood vessel walls may contain up to three distinct layers, known as tunicae, with different composition and function. The structure of a section (110) of an arterial wall is represented in FIG. 1. The innermost layer (101) of the arterial wall is the "tunica intima", which comprises a monolayer of endothelial cells (102) called endothelium, supported by a subendothelial layer, consisting of delicate connective tissue. The tunica intima is supported on an elastic membrane layer known as the "internal elastic lamina" (103). The internal elastic lamina separates the tunica intima from the next layer, the "tunica media" (104). The tunica media is a thick intermediate layer which contains smooth muscle cells (105) embedded in an extracellular matrix (ECM) in the form of collagen and other elastic fibers. The smooth muscle cells are arranged in lamellae and are disposed circularly around the blood vessel. Stimulation of the smooth muscle cells of the tunica media allows blood vessels to dilate and contract. Another elastic membrane layer, known as the "external elastic lamina" (106) separates the tunica media from the third, outermost layer of the blood vessel wall, the "tunica adventitia" (107). The tunica adventitia is mainly constituted by collagenous tissue (108) which supports fibroblasts (109) and nerves. In large vessels, the adventitia also contains the vasa vasorum, a network of small blood vessels that also penetrate into the outer portion of the media and supply the vascular wall with oxygen and nutrients.

The ECM is a molecular network, an active and dynamic structure that serves as a supporting network for blood vessels. Collagen and elastin are the two major components of the ECM, and the rest consists of other minor but relevant molecules like fibronectin, amorphous or soluble proteoglycans, leucine-rich glycoproteins and microfibrils. Cellular interaction with the ECM regulates major vascular functions such as cell adhesion, migration, proliferation and tissue architecture. The protein distribution is not linear among all the wall; some components are secreted and modulated by fibroblasts, smooth muscle cells and endothelial cells and others depend on the layer of the specific vessel's wall.

Collagen is a very stiff protein that limits vessel distention. Collagen types I and II are the main collagens in the tunica media and tunica adventitia layers in both healthy and injured arterial walls. Collagens can also interact with vascular cells. In the case of smooth muscle cells, collagens participate in cell differentiation, adhesion, migration, proliferation and apoptosis (polymerized collagens increase smooth muscle cell apoptosis by increasing the production of active MMP-1). In the case of endothelial cells, collagens prevent the production and adhesion of this cell type and also collagens affect the endothelial cell activity in vasculogenesis.

Elastin is an insoluble and hydrophobic protein. Its deposition is limited to the media layer, where it forms the dominant component of the ECM, constituting 50% of the dry weight of the blood vessel wall. Moreover, it is the largest component of the elastic fiber (~90%). In addition to mechanical integrity, elastic laminae contribute to elasticity of blood vessels. Arteries in particular are subject to extensive mechanical stress induced by arterial blood pressure and elastin enables elastic recoil of the arterial wall. In vitro, many cells exhibit migration and proliferation in response to tropoelastin, elastin degradation products and elastin peptides.

Fibronectin is a large glycoprotein that not only is a crucial protein of the ECM but also an abundant component of plasma and other fluids in the body. Fibronectin is composed of two nearly identical subunits covalently linked by a pair of disulfide bonds. Each monomer consists of three types of repeating units: type I, type II and type III. The structure of fibronectin explains why this protein mediates a wide variety of cellular interactions. Sets of repeating units constitute binding domains which bind to cell surfaces through integrins and also to other extracellular matrix molecules such as heparin, collagen/gelatin and fibrin. Fibronectin is a ligand to dozens of molecules in the integrin receptor family. These are cell-surface heterodimeric receptors which link fibronectin with the intracellular cytoskeleton, conferring structural functions to the cell. The biological activity of fibronectin includes mediation of cell adhesion, proliferation, and differentiation, as well as embryogenesis and wound healing.

Laminins are high molecular weight proteins that form one of the major components of vascular basement membranes. They are composed of a, B and γ chains which intersect to form a cross-like structure that can bind to other cell membrane and extracellular matrix molecules. Laminins are considered to be responsible for the biological functions of basement membranes such as signal transducing that control cell migration, survival, proliferation and differentiation. These biological roles are largely due to the interaction of the laminin a chains with cell surface receptors.

Damage to blood vessel walls, including the ECM components, compromises the integrity of blood vessels, triggering the development of several vascular diseases like atherosclerosis, thrombosis, aneurysms or dissections. Damage of the vessel can be caused by inflammatory processes, ECM degradation processes or external trauma. The ECM state therefore plays a fundamental role in disease progression.

Aortic dissection (AD) is the most frequent and catastrophic manifestation of the so-called acute aortic syndrome. It is a life-threatening condition caused by a tear in the intimal layer of the aorta or bleeding within the aortic wall, resulting in the separation (dissection) of the layers of the aortic wall. Blood flow forces the layers of aortic wall apart, resulting in the formation of a channel, known as a false lumen, between the layers. The condition can be fatal if the blood-filled channel ruptures through the outside of the aortic wall.

The incidence of aortic dissection is estimated at around 1 in 10,000 people per year, with a 67.5% male preponderance. The most frequent risk factors to develop aortic dissection are age, hypertension (80% of the patients), atherosclerosis (30% of the patients), previous cardiac surgery (15% of the patients) and iatrogenic causes due to previous catheter-based procedures (4% of the patients). Connective tissue genetic disorders like Marfan's and Loeys-Dietz's syndromes are strongly associated with aortic dissections. All aortic dissections present elastic fiber fragmentations and/or smooth muscle cell nuclei loss, clearly indicating an underlying malfunction of the tunica intima prior to the dissection.

AD can be triggered by two main events. The most common is the formation of an intimal tear which allows blood flow through the arterial wall and forces the separation of the layers forming an intimal flap. The second event is the rupture of the vasa vasorum, which also causes intimal bleeding and may end up with the formation of an aortic dissection. Both conditions can coexist.

The treatments to repair AD have evolved at a different speed than other vascular treatments. Until recently, surgical replacement (also called open repair) of the dissected section was the only effective treatment. Surgical repair of an aortic dissection involves the replacement of the damaged segment of the aorta with a synthetic vascular prosthesis, and valve replacement is also needed in most severe cases. The surgery is very difficult and invasive, requiring opening of the chest cavity, cardiopulmonary bypass and hypothermia, and therefore carries high rates of mortality and morbidity. Around 30% of cases require re-intervention 5 to 10 years after successful operation and, even when patients achieve full recovery from surgery, they need lifetime hypotensive medication. Despite the evident invasiveness and side effects of the intervention; it remains the preferred treatment for complicated dissections.

More recently there has been developed a method for thoracic endovascular repair of aortic dissections. Endovascular repair of an aortic dissection is a minimally-invasive intervention in which a catheter carrying a grafted stent is introduced through the femoral artery. The catheter guides the stent for deployment over the dissected segment, covering the tear and rechanneling blood flow. Endovascular repair reduces mortality and length of hospitalization compared to open surgery, but presents many limitations. The stents were originally designed to treat aortic aneurysms and using them for aortic dissection is almost off-label. In many patients, the graft does not fully conform to the patient's aorta. If the stent is under-expanded, thrombi can form and/or the graft may be displaced over time. If the stent is over-expanded, it provokes micro-injuries along the lumen that further damage the already jeopardized vessel. In either case, re-interventions in the long term are essentially unavoidable. Furthermore, grafts used both in open or endovascular repair provide a mechanical repair, but do not actively promote false lumen clotting and resorption, nor vascular remodelling and regeneration, and therefore the endothelium does not fully recover its function.

There is therefore a need in the art for devices and methods for the treatment of aortic dissection and other types of vascular damage which focus on regeneration of the damaged vascular tissue to restore its original form and function. Ideally, such methods would be minimally-invasive (i.e. suitable for endovascular deployment) and the devices would be able to cover a vascular defect to provide immediate structural repair and, after covering the defect, would promote healing, cellular regeneration and complete vessel recovery. Suitably, the device would be resorbable following complete repair and restoration of vascular function. The cellular regeneration of the vessel would prevent or minimize any graft-related side effects, thereby diminishing re-intervention rates.

BRIEF DESCRIPTION OF FIGURES

FIG. 8 is a graph showing the cell densities of human aortic endothelial cells/human smooth muscle cells in fiber layers used in the patch of the invention. The data is provided in Table 2.

FIG. 9 is a graph showing the cell velocities of human aortic endothelial cells/human smooth muscle cells in the fiber layers used in the patch of the invention. The data is provided in Table 2.

DETAILED DESCRIPTION

Figure 1:
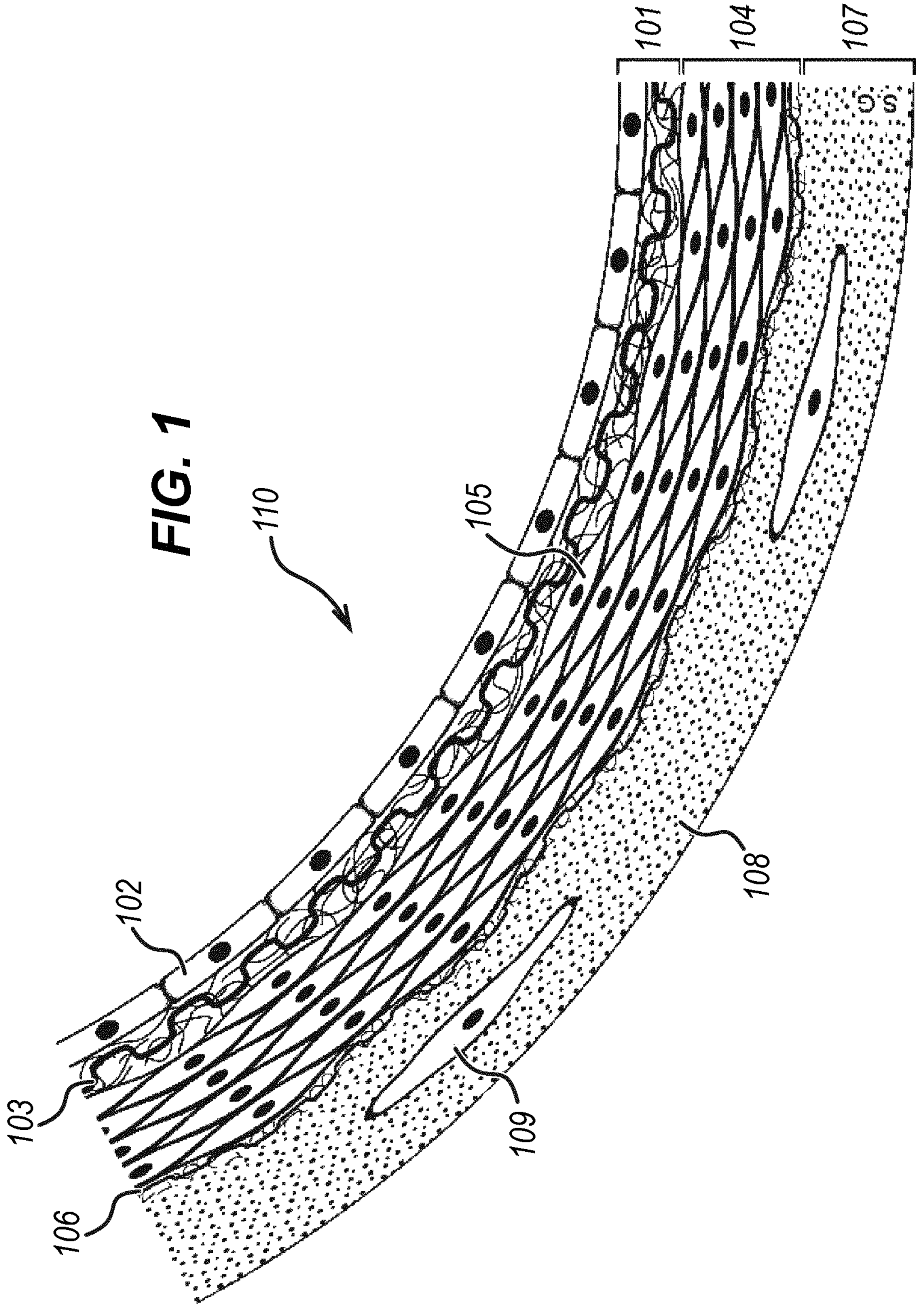
FIG. 1 is a representation of a structure of a section (110) of an arterial wall.

According to a first aspect of the invention, there is provided a vascular repair patch comprising a polymeric substrate having first and second major surfaces, wherein the substrate comprises at least:

(i) a first polymer filament layer adjacent the first major surface comprising a plurality of polymer filaments wherein the polymer filaments are oriented in parallel; and (ii) a second polymer filament layer adjacent the second major surface comprising a plurality of polymer filaments wherein the polymer filaments are oriented randomly.

The vascular repair patch therefore comprises a polymeric substrate having two different layers of polymer filaments. As a result of the different orientation of the polymer filaments, the first and second polymer filament layers have very different properties. The first polymer filament layer comprises polymer filaments oriented in parallel and is intended to form the luminal side (i.e. facing away from the blood vessel wall) of the patch when the patch is deployed for repair of a vascular defect. The second polymer filament layer comprises randomly-oriented polymer filaments and is intended to form the abluminal side (i.e. disposed against the blood vessel wall) of the patch when the patch is deployed for repair of a vascular defect. Whereas previous approaches to the repair of vascular defects involve the use of permanent patches which only cover a defect and rechannel blood flow away from the defect, it has been found that the vascular repair patch of the invention promotes repair and regeneration of healthy vasculature.

In particular, it has been found that through the orientation of the polymer filaments, the first and second polymer filament layers are able to guide the migration and proliferation of endothelial cells and smooth muscle cells, respectively, so as to repair the structure of a healthy vascular wall, More specifically, it has been found that the parallel oriented filaments of the first polymer filament layer promote two-dimensional endothelial cell migration over the abluminal side of the patch, such that an endothelial cell monolayer is formed over the patch approximately two to four weeks after the intervention. It has also been found that the randomly oriented filaments of the second polymer filament layer promote three-dimensional smooth muscle cell migration into the filament matrix over a period of around 12 months after the intervention. Controlling the filament orientation of the first and second polymer filament layers therefore optimizes the performance of the vascular repair patch in vivo.

It has been discovered that the patch according to the invention advantageously has similar viscoelastic properties to an aorta. When in use in vivo the patch of the invention complements the movement of the aorta, such that it does not undergo displacement or form kinks or folds, which could compromise the performance of the patch. Furthermore, applying the patch of the invention to an aorta does not result in a significant change in the mechanical properties of the aorta, such that it undergoes no loss of viscoelasticity and can therefore continue to function as normal during the repair process. This is in contrast to the devices of the art (e.g. grafted stents), which do not have similar viscoelastic properties to an aorta.

In a preferred embodiment of the invention, the polymeric substrate has a storage modulus, as measured by DMA (see Examples for experimental details), between 1 and 3 MPa, such as about 2 MPa. This is comparable to the elasticity of healthy human aorta, which may be in the range of around 0.75-1.25 MPa. The moduli of the patches of the invention were found to be much lower than comparative patches comprising a single layer of either randomly aligned or orientated fibers. Without wishing to be bound by theory, it is believed that the presence of an interface between the two layers in the patches of the invention provides the improved mechanical behaviour, relative to single layer patches where the mechanical properties are derived from the structure of the individual layer on its own.

The vascular repair patch is conveniently deployable by minimally-invasive endovascular methods, e.g. via a catheter.

The polymeric substrate is preferably a bioabsorbable polymeric substrate in which the polymer filaments of the first and second polymer filament layers may be formed of one or more bioabsorbable polymers. The bioabsorbable polymer filaments of the first polymer filament layer may comprise the same bioabsorbable polymer(s) as the bioabsorbable polymer filaments of the second polymer filament layer. Alternatively, the bioabsorbable polymer filaments of the first polymer filament layer may comprise different bioabsorbable polymer(s) to the bioabsorbable polymer filaments of the second polymer filament layer.

Where the polymeric substrate comprises more than one bioabsorbable polymer, the first and second polymer filament layers may comprise the same combination of bioabsorbable polymers in different weight ratios, or in the same weight ratio. Preferably, the filaments of the first and second polymer filament layers have the same polymeric composition, both in terms of the type of bioabsorbable polymer(s) used and (where appropriate) the weight ratio thereof.

The term "bioabsorbable" in the context of the invention refers to polymeric materials which can be safely absorbed by the body over a period of time. Suitable bioabsorbable polymers include bioabsorbable polyesters, for example bioabsorbable polyesters selected from one or more of polylactic acid (PLA), poly-L-lactide (PLLA), poly-D-lactide (PDLA), poly-DL-lactide (PDLLA), polyglycolic acid (PGA), polyglycolide (PG), poly(lactic-co-glycolic acid) (PLGA), poly(glycolide-co-caprolactone) (PGCL), poly (glycolide-co-trimethylene carbonate (PGA-co-TMC), polycaprolactone (PCL), poly-(L-lactide-co-caprolactone) (PLLA-co-CL), poly-(D-lactide-co-caprolactone) (PDLA-co-CL), poly-(DL-lactide-co-caprolactone (PDLLA-co-CL). Copolymers as defined herein include random, block and alternating copolymers.

Where the polymeric filaments comprise more than one type of bioabsorbable polymer, the polymeric filaments preferably each comprise a blend of the bioabsorbable polymers. However, it is not excluded that the polymeric filaments within a layer may comprise a plurality of filaments comprising a first bioabsorbable polymer or polymer blend, and another plurality of filaments comprising a second bioabsorbable polymer or polymer blend.

Preferred bioabsorbable polymers include PCL and PGLA, wherein the PGLA includes a lactide: glycolide ratio of 80:20 to 20:80, preferably about 50:50. In a preferred substrate, the polymeric filaments of at least one of the first and second polymer filament layers comprise or consist of PCL or PGLA. More preferably, the bioabsorbable substrate is one in which the polymeric filaments of both the first and second polymer filament layers comprise or consist of PCL or PGLA. Still more preferably the polymeric filaments of both the first and second polymer filament layers comprise or consist of PCL; or the polymeric filaments of both the first and second polymer filament layers comprise or consist of PGLA.

In one embodiment, the polymeric filaments of at least one of the first and second polymer filament layers comprise at least 50 wt % PCL, more preferably at least 60 wt % PCL, more preferably at least 70 wt % PCL, more preferably at least 80 wt % PCL. For instance, the polymeric filaments of at least one of the first and second polymer filament layers may comprise at least 90 wt % PCL, at least 95 wt % PCL, at least 98 wt % PCL, at least 99 wt % PCL, or 100 wt % PCL.

Optionally, the polymeric filaments of at least one of the first and second polymer filament layers comprise at least 50 wt % PCL and up to 50 wt % of PLA, PLLA, PDLA, PDLLA, PGA, PG, PLGA, PGCL, PLLA-co-CL, PDLA-co-CL, or PDLLA-co-CL. It has been found that the inclusion of a minor amount of one or more of PLA, PLLA, PDLA, PDLLA, PGA, PG, PLGA, PGCL, PLLA-co-CL, PDLA-co-CL, or PDLLA-co-CL in the polymeric filaments along with PCL decreases the bioresorption time of the bioabsorbable polymer when compared to PCL alone.

More preferably, the polymeric filaments of at least one of the first and second polymer filament layers comprise at least 50 wt % PCL and up to 50 wt % of PLGA, more preferably at least 60 wt % PCL and up to 40 wt % of PLGA, more preferably at least 70 wt % PCL and up to 30 wt % of PLGA, more preferably at least 80 wt % PCL and up to 20 wt % of PLGA. As noted above, the inclusion of PLGA provides a preferred way to decrease the bioresorption time of the bioabsorbable polymer when compared to PCL alone. The ratio of lactide to glycolide monomers in the PLGA is preferably from 80:20 to 20:80, and more preferably about 50:50, although other ratios may be selected according to the required bioresorption properties.

Optionally, the polymeric filaments of at least one of the first and second polymer filament layers comprise a blend of at least 50 wt % PCL or PGLA, more preferably at least 60 wt % PCL or PGLA, more preferably at least 70 wt % PCL or PGLA, more preferably around 80 wt % PCL or PGLA and at least one of gelatin, squalene and triethyl citrate.

For example, the polymeric filaments of at least one of the first and second polymer filament layers may comprise a blend of at least 70 wt % PCL or PGLA and up to 30 wt % gelatin, more preferably at least 80 wt % PCL or PGLA and up to 20 wt % gelatin. For instance, the polymeric filaments of at least one of the first and second polymer filament layers may comprise 80 wt % PCL or PGLA and 20 wt % gelatin.

Alternatively, the polymeric filaments of at least one of the first and second polymer filament layers comprise a blend of at least 80 wt % PCL or PGLA and up to 20 wt % squalene, more preferably at least 85 wt % PCL or PGLA and up to 15 wt % squalene. For instance, the polymeric filaments of at least one of the first and second polymer filament layers may comprise 85 wt % PCL or PGLA and 15 wt % squalene. It has been found that the inclusion of squalene in the polymeric filaments reduces stiffness and improves viscoelasticity when compared to PCL or PGLA alone.

Alternatively, the polymeric filaments of at least one of the first and second polymer filament layers comprise a blend of at least 80 wt % PCL or PGLA and up to 20 wt % triethyl citrate, more preferably at least 85 wt % PCL or PGLA and up to 15 wt % triethyl citrate. For instance, the polymeric filaments of at least one of the first and second polymer filament layers may comprise 85 wt % PCL or PGLA and 15 wt % triethyl citrate. It has also been found that the inclusion of triethyl citrate in the polymeric filaments reduces stiffness and further improves viscoelasticity when compared to PCL or PGLA alone.

The bioabsorbable polymer is suitably selected such that bioabsorption slowly takes place over a period of one to two years following the surgical intervention. It has been found that this timescale allows for the vascular defect to repair sufficiently that the additional mechanical support from the patch is no longer required to cover the defect and reinforce the regenerating vascular wall.

The polymeric filaments of the first and second polymer filament layers suitably have an average filament diameter in the range of from 1 to 20 μm, more preferably from 1 to 15 μm, more preferably from 2 to 10 μm, more preferably from 3 to 8 μm, more preferably about 5 μm. As used herein, average filament diameter refers to the mean number average of the diameters of at least 25 filaments, wherein filament diameters are determined by measurements taken perpendicular to the long axis of filaments in a scanning electron microscopy (SEM) image (see Examples for the experimental details).

The filament diameters of the first and second polymer filament layers may optionally form a bimodal distribution with one peak in the range of from 0.2 to 2 μm and a second peak in the range of from 2.5 to 10 μm. It has been found that the inclusion of filaments of smaller diameter provides an improved matrix for the initial colonisation of smooth muscle cells. These smaller diameter filaments are then bioabsorbed as soon as the extracellular matrix is repaired.

The filaments preferably have a consistent diameter along their length with a variation in diameter of no more than 20% of the largest diameter, preferably no more than 10% of the largest diameter.

The polymeric filaments are preferably electrospun filaments. Electrospinning is a method of fabricating polymer filaments in which an electrical force is used to draw charged threads of polymer solutions from a spinning tip towards a grounded collector. The grounded collector comprises a conductive material which is grounded to create a potential difference with the spinning tip and draw the polymer solution from the spinning tip. The collector may have a number of configurations, such as a planar plate (producing a randomly oriented web of electrospun filaments) or a rotating drum (producing an aligned web of electrospun filaments, with the degree of alignment depending on the rotational speed of the drum). The use of electrospun filaments provides a simple means of obtaining the required parallel-oriented and randomly-oriented layers of the vascular repair patch. In addition, it has been found that electrospinning the polymer filaments reduces the stiffness of the patch, providing a patch with similar mechanical properties to a healthy blood vessel.

In a preferred embodiment, the polymeric substrate has a Young's modulus in the range of from 0.5 to 3.0 MPa. This compares to a range of around 0.3 to 10 MPa for the human aorta (the value of 0.3 MPa representing a healthy, young aorta; and the value of 10 MPa representing an aged and unhealthy aorta).

Figure 2:
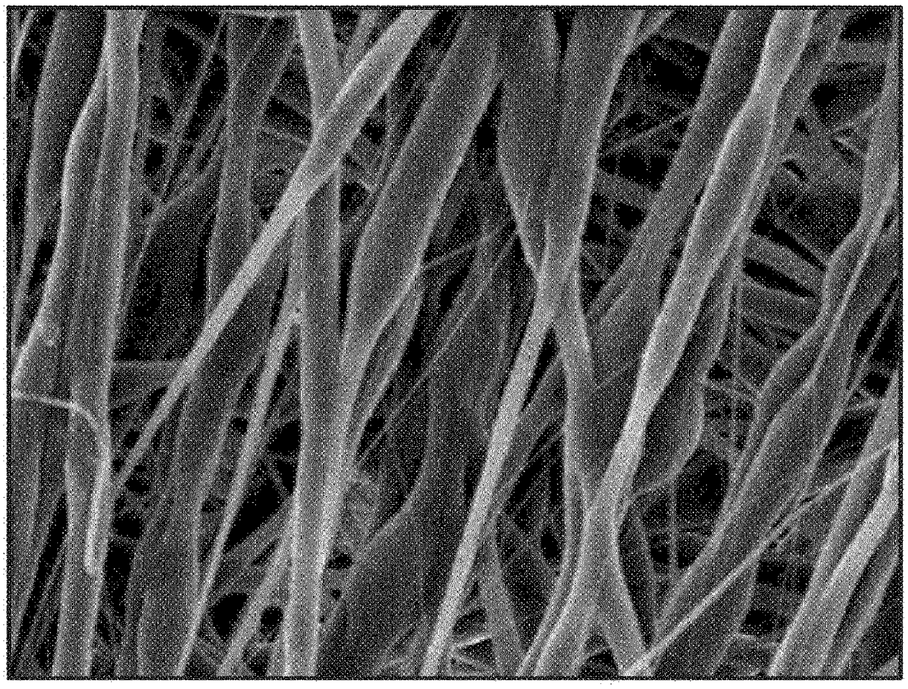
FIG. 2 is an SEM image of parallel oriented PCL fibers.
Figure 3:
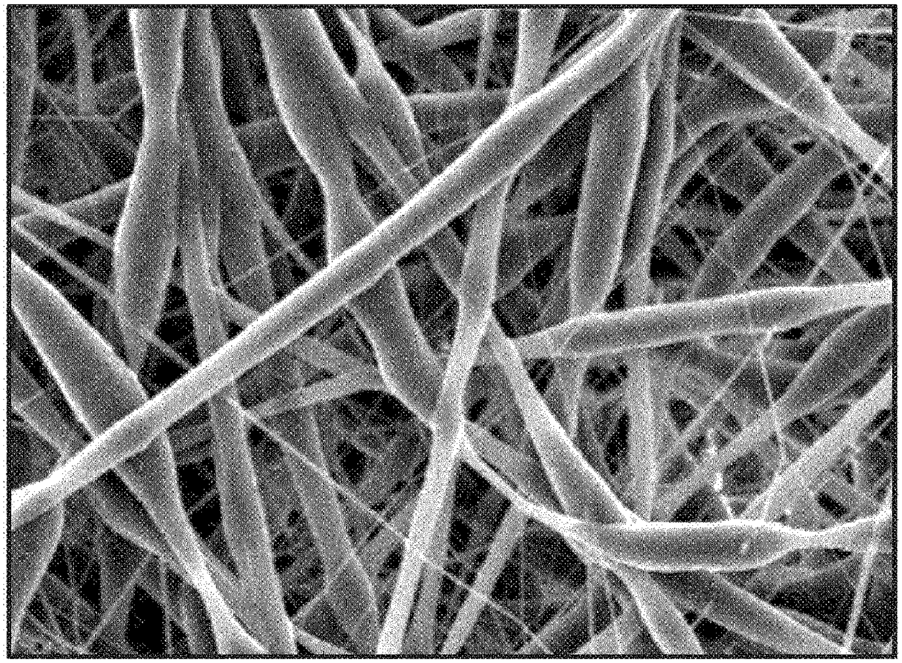
FIG. 3 is an SEM image of randomly oriented PCL fibers.

An SEM image of parallel oriented PCL fibers is shown in FIG. 2 and an SEM image of randomly oriented PCL filaments is shown in FIG. 3.

As used herein, the terms "oriented in parallel" and "parallel orientation" mean that the filaments of the first polymer filament layer are oriented with a standard deviation of no more than 36° (i.e. 20% of) 180° and most preferably no more than 18° (i.e. 10% of) 180°.

As used herein, the terms "oriented randomly" and "random orientation" mean that the filaments of the second polymer filament layer are oriented with a standard deviation of at least 45° (i.e. 25% of) 180° and more preferably at least 54° (i.e. 30% of) 180°, more preferably at least 63° (i.e. 35% of) 180°, more preferably at least 72° (i.e. 40% of) 180°, more preferably at least 81° (i.e. 45% of) 180°, more preferably at least 90° (i.e. 50% of) 180°.

Preferably, the filaments of the first polymer filament layer are oriented with a standard deviation of no more than 36° and the filaments of the second polymer filament layer are oriented with a standard deviation of at least 45°, more preferably at least 54°, more preferably at least 63°, more preferably at least 72°.

Still more preferably, the filaments of the first polymer filament layer are oriented with a standard deviation of no more than 18° and the filaments of the second polymer filament layer are oriented with a standard deviation of at least 63°, more preferably at least 72°, more preferably at least 81°, more preferably at least 90°.

Filament orientation in each layer as described herein refer to measurements determined using the standard, open source ImageJ plug-in, OrientationJ, which creates an orientation distribution output. For example, the measurements may be determined using ImageJ (v1.52i).

The second polymer filament layer suitably has an average porosity of from 30 to 70%, preferably from 40 to 60%, more preferably around 50%.

The second polymer filament layer suitably has an average pore diameter in the range of from 50 to 300 μm, more preferably from 100 to 250 μm, more preferably from 150 to 200 μm. The pore structure formed by the randomly oriented polymeric filaments of the second polymer filament layer provides a plurality of channels or passageways for the migration and growth of smooth muscle cells. Smooth muscle cells have a side diameter in the range of from 5 to 100 μm and therefore with the preferred pore diameters set out above, each pore can typically accommodate networks of from 2 to 5 interconnected cells within the randomly oriented filament network of the second polymer filament layer.

Porosity and pore diameters as described herein refer to measurements determined using the standard, open source ImageJ plug-in, DiameterJ, which creates a pore diameter distribution output. The term "porosity" as defined herein is calculated on an areal basis (pore area/total area). For example, the measurements may be determined using ImageJ (v1.52i).

Each of the first and second polymer filament layers preferably has a thickness that is independently in the range of from 10 μm to 200 μm, more preferably from 20 μm to 100 μm, more preferably from 30 μm to 70 μm, for example about 50 μm.

The vascular repair patch of the invention is substantially two-dimensional/planar in form, with the length and width of the first and second major surfaces being substantially larger than the thickness of the patch.

The total thickness of the vascular repair patch of the invention is preferably in the range of 20 μm to 500 μm, more preferably from 50 μm to 200 μm, more preferably from 50 μm to 150 μm, for example about 100 μm.

The length and width of the vascular repair patch of the invention are preferably each independently in the range of from 10 to 50 mm, more preferably from 20 to 40 mm. For example, the patch may have a length of from 25 to 35 mm and a width of from 15 to 25 mm, and particularly preferred dimensions of the patch for aortic repair include a length of 30 mm and a width of 20 mm.

The vascular repair patch of the invention may have any shape suitable for deployment over a vascular defect. For example, the patch may be square, rectangular, circular, or oval.

In a preferred embodiment, the filaments of the first polymer filament layer lie substantially parallel to the length direction of the vascular repair patch and the length of the patch is greater than the width, for instance at least 20% or at least 50% greater than the width. In this configuration, the luminal surface of the patch comprises filaments that may be oriented parallel to the flow of blood through the damaged vessel following deployment of the patch. In this configuration, the parallel oriented filaments provide minimal resistance to blood flow over the surface of the vascular repair patch, and this reduces the possibility of displacement or detachment of the patch.

The first polymer filament layer of the vascular repair patch preferably comprises one or more extracellular matrix compounds. As noted above, the extracellular matrix is a molecular network found in the vascular wall, and it has been found that providing extracellular matrix compounds on the luminal surface of the vascular repair patch promotes endothelial cell migration over the abluminal side of the patch, such that an endothelial cell monolayer is formed over the patch. The extracellular matrix compounds suitably comprise one or more of collagen (particularly collagen types I and II), elastin, fibronectin, laminins, VE-cadherin, vitronectin, integrins, heparan sulfate, chondroitin sulfate, kétaran sulfate, hyaluronic acid, as well as peptide sequences most relevant to cell adhesion and migration, for example Arg-Gly-Asp (RGD), Arg-Glu-Asp-Val (REDV), Tyr-Ile-Gly-Ser-Arg (YIGSR) and the like. The extracellular matrix compounds may be hydrogen bonded or covalently bonded to the polymeric filaments of the first polymer filament layer to prevent wash-off due to vascular flow.

Preferably, the extracellular matrix compounds are selected from fibronectin, laminins (particularly laminin-511) and VE-cadherin. A particularly preferred extracellular matrix compound is fibronectin.

The first polymer filament layer of the vascular repair patch preferably comprises the one or more extracellular matrix compounds in an areal amount of from 0.5 $\mu g/cm^2$ to 100 $\mu g/cm^2$, based on the surface area of the first surface of the patch. More preferably, the first polymer filament layer of the vascular repair patch comprises the one or more extracellular matrix compounds in an areal amount of from 1 $\mu g/cm^2$ to 50 $\mu g/cm^2$, more preferably from 1.5 $\mu g/cm^2$ to 20 $\mu g/cm^2$, more preferably from 2 $\mu g/cm^2$ to 15 $\mu g/cm^2$, more preferably from 2.5 $\mu g/cm^2$ to 10 $\mu g/cm^2$, more preferably from 3 $\mu g/cm^2$ to 7 $\mu g/cm^2$, based on the surface area of the first surface of the patch.

The second surface of the vascular repair patch may be provided with a coating of a suitable biocompatible adhesive to facilitate secure attachment of the patch to the vascular wall and withstand vascular flow. Suitable biocompatible adhesives are well-known in the art and include synthetic adhesives (such as acrylates, cyanoacrylates and polyurethanes) and natural polymers (such as hyaluronic acids, celluloses and alginates). The mechanism of adhesion may include the formation of covalent bonds and/or hydrogen bonds between the adhesive and the vascular tissue. In some embodiments of the invention, the biocompatible adhesive is ethyl cyanoacrylate, a mixture of ethyl cyanoacrylate and silica particles, or butyl cyanoacrylate.

Alternatively, or in addition, the second surface of the vascular repair patch may be provided with a physical securement means, such as a plurality of microneedles, to facilitate secure attachment of the patch to the vascular wall and withstand vascular flow. The microneedles are suitably formed of a bioabsorbable material, for instance one or more of the bioabsorbable polymeric materials described above.

The second polymer filament layer may optionally comprise one or more thrombogenic agents, particularly one or more components of the coagulation cascade, for example tissue factor (TF, or Factor III), Factor VII, Factor X and Fibrin. A preferred thrombogenic agent is TF. It has been found that the incorporation of thrombogenic agents, such as TF, into the second polymer filament layer of the vascular repair patch promotes smooth muscle cell migration into the randomly-oriented filament matrix.

The second polymer filament layer of the vascular repair patch preferably comprises the one or more thrombogenic agents in an areal amount of from 0.5 $\mu g/cm^2$ to 100 $\mu g/cm^2$, based on the surface area of the second surface of the patch. More preferably, the first polymer filament layer of the vascular repair patch comprises the one or more thrombogenic agents in an areal amount of from 1 $\mu g/cm^2$ to 50 $\mu g/cm^2$, more preferably from 1.5 $\mu g/cm^2$ to 20 $\mu g/cm^2$, more preferably from 2 $\mu g/cm^2$ to 15 $\mu g/cm^2$, more preferably from 2.5 $\mu g/cm^2$ to 10 $\mu g/cm^2$, more preferably from 3 $\mu g/cm^2$ to 7 $\mu g/cm^2$, based on the surface area of the first surface of the patch.

Figure 4:
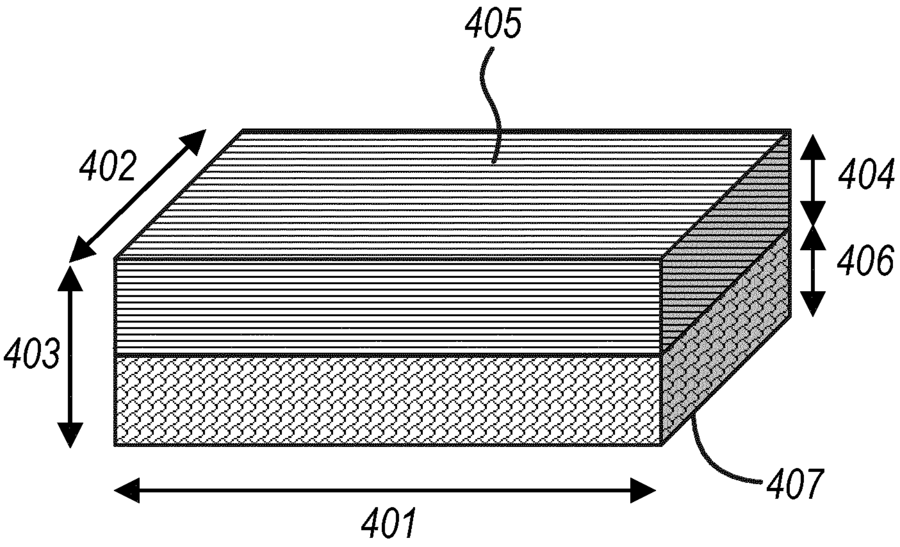
FIG. 4 schematically depicts a vascular repair patch of the first aspect of the invention.
Figure 5:
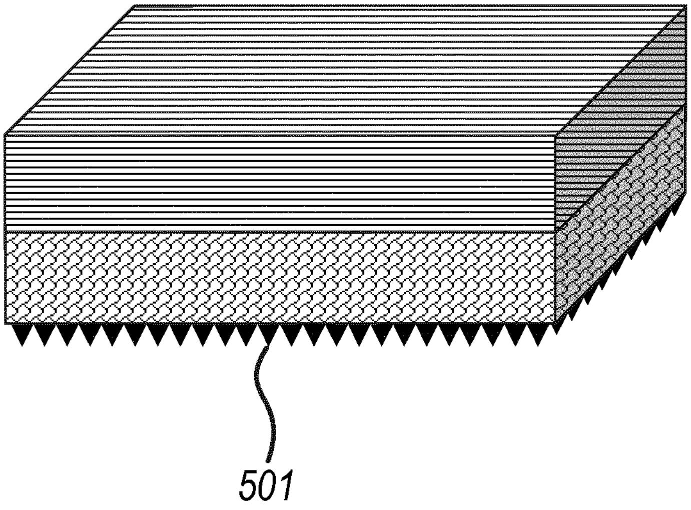
FIG. 5 shows a modification of the patch in which the second major surface is provided with a plurality of microneedles (501).

The vascular repair patch of the first aspect of the invention is described schematically with reference to FIG. 4. FIG. 4 shows a patch having a length (401), width (402) and thickness (403), wherein the length and thickness are each substantially larger than the thickness such that the patch is substantially two-dimensional/planar in form. The patch has a first polymer filament layer (404) adjacent the first major surface (405) and a second polymer filament layer (406) adjacent the second major surface (407). The first polymer filament layer comprises a plurality of parallel oriented filaments and the second polymer filament layer comprises a plurality of randomly oriented filaments. FIG. 5 shows a modification of the patch in which the second major surface is provided with a plurality of microneedles (501).

According to a second aspect of the invention, there is provided a vascular repair patch comprising a polymeric substrate having first and second major surfaces, wherein the polymeric substrate comprises at least one polymer filament layer adjacent the first major surface; and wherein one or more extracellular matrix compounds are disposed on the first major surface of the polymeric substrate.

In accordance with the second aspect of the invention, the extracellular matrix compounds are suitably selected from one or more of collagen (particularly collagen types I and II), elastin, fibronectin, laminins, VE-cadherin vitronectin, integrins, heparan sulfate, chondroitin sulfate, ketaran sulfate, hyaluronic acid, as well as peptide sequences most relevant to cell adhesion and migration, for example Arg-Gly-Asp (RGD), Arg-Glu-Asp-Val (REDV), Tyr-Ile-Gly-Ser-Arg (YIGSR) and the like. The extracellular matrix compounds may be covalently bonded to the polymeric filaments of the first polymer filament layer to prevent wash-off due to vascular flow. Preferably, the extracellular matrix compounds are selected from fibronectin, laminins (particularly laminin-511) and VE-cadherin. A particularly preferred extracellular matrix compound is fibronectin.

The at least one polymer filament layer preferably comprises the one or more extracellular matrix compounds in an areal amount of from 0.5 $\mu g/cm^2$ to 100 $\mu g/cm^2$, based on the surface area of the first surface of the patch. More preferably, the first polymer filament layer of the vascular repair patch comprises the one or more extracellular matrix compounds in an areal amount of from 1 $\mu g/cm^2$ to 50 $\mu g/cm^2$, more preferably from 1.5 $\mu g/cm^2$ to 20 $\mu g/cm^2$, more preferably from 2 $\mu g/cm^2$ to 15 $\mu g/cm^2$, more preferably from 2.5 $\mu g/cm^2$ to 10 $\mu g/cm^2$, more preferably from 3 $\mu g/cm^2$ to 7 $\mu g/cm^2$, based on the surface area of the first surface of the patch.

The at least one polymer filament layer preferably comprises a plurality of polymer filaments, wherein the polymer filaments are oriented in parallel. Optionally, the length of the patch is greater than the width, for instance at least 20% or at least 50% greater than the width, and the filaments of the first polymer filament layer lie substantially parallel to the length direction of the vascular repair patch. In this configuration, the luminal surface of the patch comprises filaments that may be oriented parallel to the flow of blood through the damaged vessel following deployment of the patch. In this configuration, the parallel oriented filaments provide minimal resistance to blood flow over the surface of the vascular repair patch, and this reduces the possibility of displacement or detachment of the patch.

The polymeric substrate is preferably a bioabsorbable polymeric substrate in which the polymer filaments of the at least one polymer filament layer may be formed of one or more bioabsorbable polymers. In accordance with the second aspect of the invention, the polymer filaments may have any of the features described in relation to the first aspect of the invention. Any features of the polymer filaments identified as "preferred" in the context of the first aspect of the invention are also preferred in the context of the second aspect of the invention.

The at least one polymer filament layer preferably has a thickness that is in the range of from 10 μm to 200 μm, more preferably from 20 μm to 100 μm, more preferably from 30 μm to 70 μm, for example about 50 μm.

The second surface of the vascular repair patch may be provided with a coating of a suitable biocompatible adhesive to facilitate secure attachment of the patch to the vascular wall and withstand vascular flow. Suitable biocompatible adhesives are described above. Alternatively, or in addition, the second surface of the vascular repair patch may be provided with a physical securement means as described above.

In accordance with the first and second aspects of the invention, the vascular repair patch may be provided with markings to indicate the direction of orientation of the parallel oriented filaments. These markings may take the form of a printed marking, or embossing/indentation in the surface of the patch. Alternatively, the vascular repair patch may be provided in a package, wherein the package is provided with markings to indicate the direction of orientation of the parallel oriented filaments.

According to a third aspect of the invention, there is provided a vascular repair patch comprising a polymeric substrate having first and second major surfaces, wherein the polymeric substrate comprises at least one polymer filament layer adjacent the second major surface; and wherein one or more thrombogenic agents are disposed on the second major surface of the polymeric substrate.

The one or more thrombogenic agents may be selected from one or more components of the coagulation cascade, for example tissue factor (TF, or Factor III), Factor. VII, Factor X and Fibrin. A preferred thrombogenic agent is TF.

The at least one polymer filament layer preferably comprises the one or more thrombogenic agents in an areal amount of from 0.5 $\mu g/cm^2$ to 100 $\mu g/cm^2$, based on the surface area of the second surface of the patch. More preferably, the first polymer filament layer of the vascular repair patch comprises the one or more thrombogenic agents in an areal amount of from 1 $\mu g/cm^2$ to 50 $\mu g/cm^2$, more preferably from 1.5 $\mu g/cm^2$ to 20 $\mu g/cm^2$, more preferably from 2 $\mu g/cm^2$ to 15 $\mu g/cm^2$, more preferably from 2.5 $\mu g/cm^2$ to 10 $\mu g/cm^2$, more preferably from 3 $\mu g/cm^2$ to 7 $g/cm^2$, based on the surface area of the first surface of the patch.

The at least one polymer filament layer preferably comprises a plurality of polymer filaments, wherein the polymer filaments are randomly oriented.

The polymeric substrate is preferably a bioabsorbable polymeric substrate in which the polymer filaments of the at least one polymer filament layer may be formed of one or more bioabsorbable polymers. In accordance with the third aspect of the invention, the polymer filaments may have any of the features described in relation to the first aspect of the invention. Any features of the polymer filaments identified as "preferred" in the context of the first aspect of the invention are also preferred in the context of the third aspect of the invention.

The at least one polymer filament layer preferably has a thickness that is in the range of from 10 μm to 200 μm, more preferably from 20 μm to 100 μm, more preferably from 30 μm to 70 μm, for example about 50 μm.

The second surface of the vascular repair patch may be provided with a coating of a suitable biocompatible adhesive to facilitate secure attachment of the patch to the vascular wall and withstand vascular flow. Suitable biocompatible adhesives are described above. Alternatively, or in addition, the second surface of the vascular repair patch may be provided with a physical securement means as described above.

In accordance with the first, second and third aspects of the invention, the vascular repair patch may be provided with markings to indicate the first and second surfaces thereof. As noted above, the patch of the invention is preferably deployed such that the first surface forms the luminal side of the patch and the second surface forms the abluminal side of the patch. Alternatively, the vascular repair patch may be provided in a package, wherein the package is provided with markings to indicate the direction of orientation of the parallel oriented filaments.

In the case that the patch comprises parallel oriented filaments, these marking on the patch or on a packaging for the patch may simultaneously indicate both the direction of orientation of the parallel oriented filaments and distinguish the first and second surfaces of the patch.

Optionally, the vascular repair patch according to the first, second or third aspects of the invention can be coated with one or more antibiotics to reduce the risk of post-implant infection.

According to a fourth aspect of the invention, there is provided a method of treating a vascular defect, the method comprising positioning a vascular repair patch according to any of the first, second and third aspects of the invention across the vascular defect such that the vascular repair patch conforms to the inside of the vascular wall.

By "across" the vascular defect, it is meant generally that the vascular repair patch will extend in two dimensions to completely cover the vascular defect and to substantially prevent blood flow into the vascular defect. Where the vascular repair patch comprises parallel oriented filaments, it is preferred that the patch is deployed such that the parallel oriented filaments adjacent the luminal surface of the patch are oriented parallel to the flow of blood through the damaged vessel following deployment of the patch. This reduces resistance to blood flow over the surface of the vascular repair patch, and this reduces the possibility of displacement or detachment of the patch.

The vascular defect may be a tear in a vascular wall, for example the wall of an artery or vein. More preferably, the vascular defect is an aortic dissection.

In accordance with the fourth aspect of the invention, the vascular repair patch is preferably deployed by an endovascular delivery system, e.g. using a catheter or guide wire to deploy the vascular repair patch. The delivery system should be able to apply sufficient force against the patch to facilitate securement of the patch to the vascular wall across the vascular defect and to subsequently release the patch.

The vascular repair patch is preferably deployed such that the first surface forms the luminal side of the patch and the second surface forms the abluminal side of the patch. Typically, the vascular repair patch will be held in place by a bioadhesive on the second surface and/or by a physical securement means, such as a plurality of microneedles, formed on the second surface of the vascular repair patch. However, it is not excluded that the patch may be secured in position by an external securement means, such as a stent.

Figures 6A, 6B, 6C, 6D:
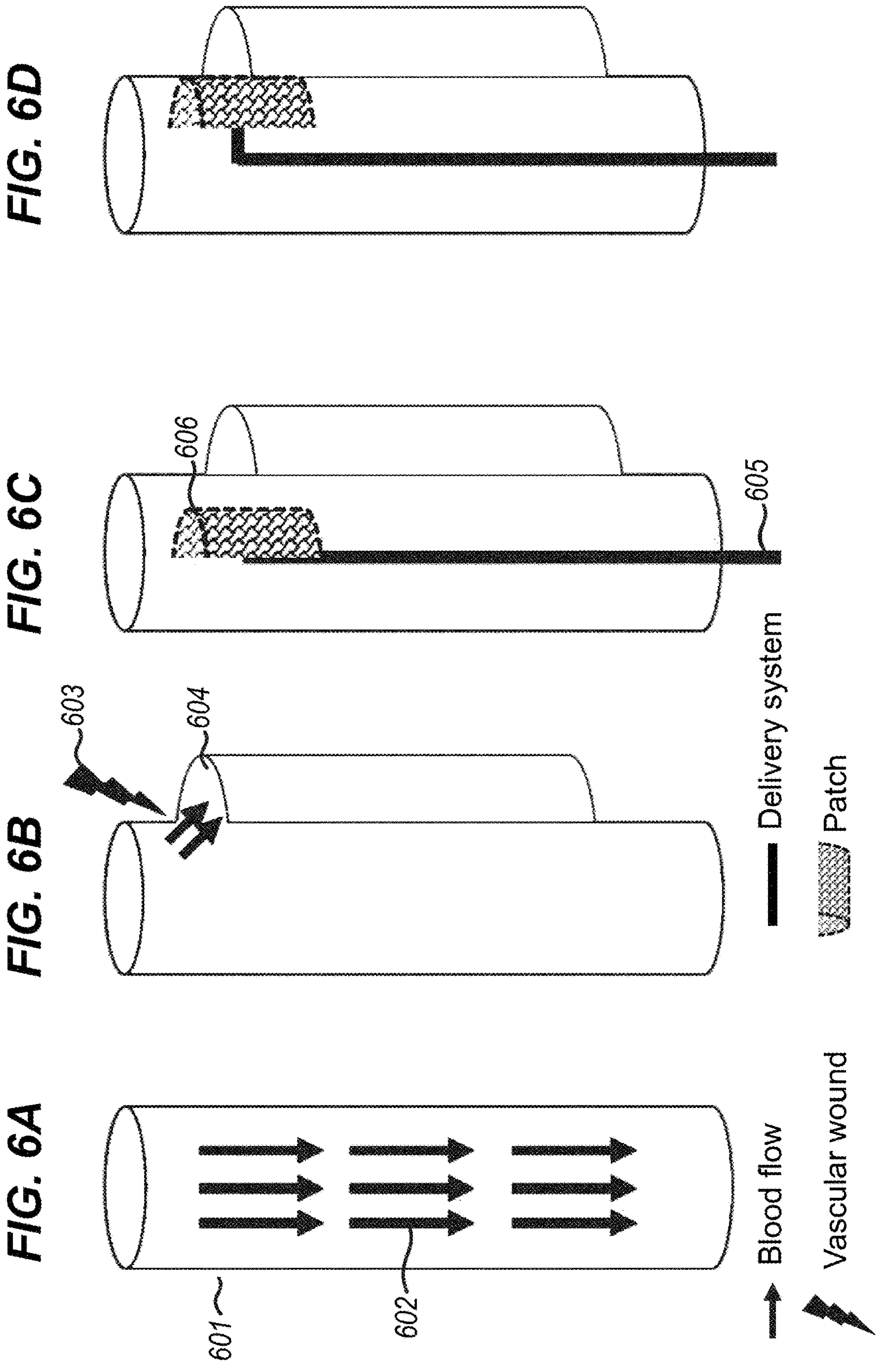
FIGS. 6A to 6D schematically depict a method of the invention.

The method of the invention is described schematically with reference to FIGS. 6A to 6D. FIG. 6A represents an intact artery (601) with the direction of blood flow represented by arrows (602). FIG. 6B shows the formation of a vascular defect (603) and the formation of a false lumen (604). FIG. 6C shows a catheter (605) carrying a vascular repair patch (606) according to the invention to the site of the vascular defect, and FIG. 6D shows the deployment of the patch over the vascular defect.

Figure 7:
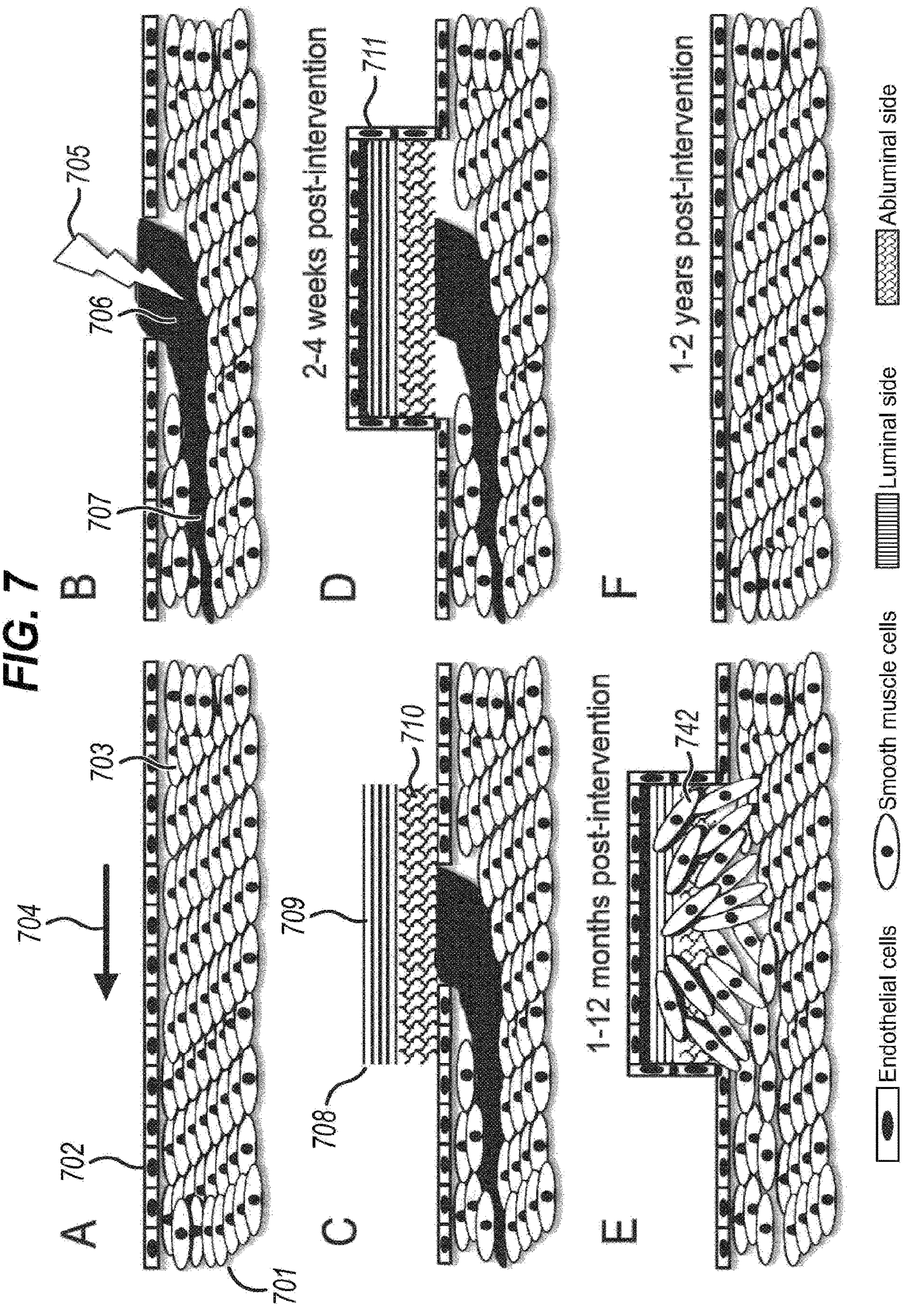
FIGS. 7A to 7F described depict the operation of the vascular repair patch of the invention.

The operation of the vascular repair patch of the invention is described schematically with reference to FIGS. 7A to 7F. FIG. 7A shows a healthy blood vessel (701), including the endothelium (702), of the tunica intima and the smooth muscle cells (703) of the tunica media (the tunica adventitia is not shown). The direction of blood flow is indicated by the arrow (704). FIG. 7B shows the formation of a vascular defect (705) and the ingress of arterial blood (706) forming a false lumen (707) between the layers of the vascular wall. FIG. 7C shows a vascular repair patch (708) according to the invention deployed over the vascular defect (705), the patch comprising a first polymer filament layer (709) comprising a plurality of polymer filaments in parallel; and a second polymer filament layer (710) comprising a plurality of polymer filaments oriented randomly.

The patch is deployed with the first major (luminal) surface of the first substrate layer (709) facing the internal lumen of the blood vessel, and the second major (abluminal) surface of the second substrate layer comprising randomly oriented filaments disposed against the vascular wall. FIG. 7D depicts the vascular repair patch of the invention at around two to four weeks following surgical intervention, by which time a monolayer of epithelial cells (711) is formed over the luminal surface. FIG. 7E depicts the vascular repair patch of the invention at around one to twelve months following surgical intervention, by which time smooth muscle cells (712) have migrated into the second polymer filament layer of the device. Finally, FIG. 7F depicts a healthy, regenerated blood vessel formed following complete cellular regeneration of the vascular wall and bioabsorption of the vascular repair patch.

According to a fifth aspect of the invention, there is provided an extracellular matrix compound for use in a method of treating a vascular defect, wherein the extracellular matrix compound is in the form of a vascular repair patch according to the first or second aspects of the invention, wherein the method comprises positioning the vascular repair patch across the vascular defect such that the vascular repair patch conforms to the inside of the vascular wall.

The extracellular matrix compound may be selected from one or more of collagen (particularly collagen types I and II), elastin, fibronectin, laminins, VE-cadherin, vitronectin, integrins, heparan sulfate, chondroitin sulfate, ketaran sulfate, hyaluronic acid, and peptide sequences selected from example Arg-Gly-Asp (RGD), Arg-Glu-Asp-Val (REDV), Tyr-Ile-Gly-Ser-Arg (YIGSR).

Preferably, the extracellular matrix compound is selected from fibronectin, laminins (particularly laminin-511) and VE-cadherin. More preferably, the extracellular matrix compound is fibronectin.

According to a sixth aspect of the invention, there is provided a thrombogenic agent for use in a method of treating a vascular defect, wherein the thrombogenic agent is in the form of a vascular repair patch according to the first or third aspects of the invention, wherein the method comprises positioning the vascular repair patch across the vascular defect such that the vascular repair patch conforms to the inside of the vascular wall.

The thrombogenic agent may be selected from one or more components of the coagulation cascade, for example tissue factor (TF, or Factor III), Factor VII, Factor X and Fibrin. Preferably, the thrombogenic agent is TF.

According to a seventh aspect of the invention, there is provided a method of making a vascular repair patch according to the first aspect of the invention, the method comprising:

(a) providing a polymeric substrate having first and second major surfaces by forming at least one of (i) a first polymer filament layer comprising a plurality of polymer filaments wherein the polymer filaments are oriented in parallel; and (ii) a second polymer filament layer comprising a plurality of polymer filaments wherein the polymer filaments are oriented randomly.

The method may optionally further comprise the steps of:

(b) applying one or more extracellular matrix compounds onto the first major surface of the polymeric substrate; and/or (c) applying one or more thrombogenic agents onto the second major surface of the polymeric substrate.

The method of the seventh aspect of the invention may have any of the preferred/optional features already set out in relation to the first aspect of the invention. In particular, the type and dimensions of the polymeric filaments, and the type and amount of extracellular matrix compounds and/or thrombogenic agents may be as described with reference to the first aspect of the invention. Similarly, the polymeric substrate may have any of the dimensions, shape or physical properties described with reference to the first aspect of the invention.

Step (a) may comprise forming the first polymer filament layer and/or the second polymer filament layer by electrospinning. The collector may have a number of configurations, such as a planar plate (producing a randomly oriented web of electrospun filaments) or a rotating drum (producing an aligned web of electrospun filaments, with the degree of alignment depending on the rotational speed of the drum). For example, the polymer (e.g. a bioabsorbable polymer as described above) may be dissolved in a solvent at a concentration ranging from 5% to 15% w/v.

Suitable solvents include chloroform, a mixture of chloroform and dimethylformamide (e.g. 90 vol % chloroform and 10 vol % dimethylformamide), or a mixture of chloroform and dimethylsulfoxide (e.g. 90 vol % chloroform and 10 vol % dimethylsulfoxide).

The polymer solution is then placed in a syringe pump and propelled towards the collector at a volumetric flow in the range of 500 to 5,000 μL/h. The syringe pump is typically placed at a distance of from 15 to 30 cm from the collector and a voltage potential ranging between 20 and 30 KV is applied between the syringe and the collector. The electrospun filament web thus formed is allowed to dry before being removed from the collector.

The first and second polymer filament layers may optionally be formed separately and subsequently joined together. Alternatively, the first and second polymer filament layers may be formed by sequential electrospinning of each layer.

The polymeric substrate may be subjected to a plasma treatment prior to steps (b) and/or (c) to increase adhesion of the extracellular matrix compounds and/or the thrombogenic agents to the patch, and to prevent these components being washed out of the patch by blood flow. The plasma treatment may be carried out using atmospheric pressure corona discharge or under vacuum, using gases that may include air, oxygen, nitrogen, argon and combinations thereof. A preferred plasma treatment uses oxygen or a mixture of oxygen and argon at a pressure of ca. 0.15 mbar.

The extracellular matrix compounds and/or the thrombogenic agents may be applied to the polymeric substrate by any suitable method, for instance, an aqueous solution of the extracellular matrix compounds and/or the thrombogenic agents applied using spray applicator, roller applicator, or by dipping a surface of the substrate into the aqueous solution.

In one preferred method, the first surface of the polymeric substrate is dipped into an aqueous solution comprising ca. 100 μg/mL of one or more extracellular matrix compounds to impregnate the first substrate layer with the solution of the one or more extracellular matrix compounds. The impregnated substrate is then allowed to dry to provide a dispersion of the one or more extracellular matrix compounds in the first substrate layer.

In another preferred method, the second surface of the polymeric substrate is dipped into an aqueous solution comprising ca. 100 μg/mL of one or more thrombogenic agents to impregnate the second substrate layer with the solution of one or more thrombogenic agents. The impregnated substrate is then allowed to dry to provide a dispersion of the one or more thrombogenic agents in the second substrate layer.

The method may further comprise providing a coating of a biocompatible adhesive on the second surface of the polymeric substrate. Suitable biocompatible adhesives are as described for the first aspect of the invention.

The method may further comprise providing a physical securement means, such as a plurality of microneedles, on the second surface of the polymeric substrate.

According to an eighth aspect of the invention, there is provided a method of making a vascular repair patch according to the second aspect of the invention, the method comprising:

(a) providing a polymeric substrate having first and second major surfaces by forming at least one polymer filament layer comprising a plurality of polymer filaments wherein the polymer filaments are oriented in parallel; and (b) applying one or more extracellular matrix compounds onto the first major surface of the polymeric substrate.

The method of the eighth aspect of the invention may have any of the preferred/optional features already set out in relation to the first aspect of the invention. In particular, the type and dimensions of the polymeric filaments, and the type and amount of extracellular matrix compounds may be as described with reference to the first aspect of the invention. Similarly, the polymeric substrate and the at least one polymer filament layer may have any of the dimensions, shape or physical properties described with reference to the polymeric substrate and the first polymer filament layer described in relation to the first aspect of the invention.

Step (a) may comprise forming the at least one polymer filament layer by electrospinning, as described above in relation to the seventh aspect of the invention.

The polymeric substrate may be subjected to a plasma treatment prior to step (b), as described above in relation to the seventh aspect of the invention.

The extracellular matrix compounds may be applied to the polymeric substrate by any suitable method, for instance, an aqueous solution of the extracellular matrix compounds may be applied using spray applicator, roller applicator, or by dipping a surface of the substrate into the aqueous solution.

In one preferred method, the first surface of the polymeric substrate is dipped into an aqueous solution comprising ca. 100 μg/mL of one or more extracellular matrix compounds to impregnate the first substrate layer with the solution of the one or more extracellular matrix compounds. The impregnated substrate is then allowed to dry to provide a dispersion of the one or more extracellular matrix compounds in the first substrate layer.

The method may further comprise providing a coating of a biocompatible adhesive on the second surface of the polymeric substrate. Suitable biocompatible adhesives are as described for the first aspect of the invention.

The method may further comprise providing a physical securement means, such as a plurality of microneedles, on the second surface of the polymeric substrate.

According to a ninth aspect of the invention, there is provided a method of making a vascular repair patch according to the third aspect of the invention, the method comprising:

(a) providing a polymeric substrate having first and second major surfaces by forming at least one polymer filament layer comprising a plurality of polymer filaments wherein the polymer filaments are oriented randomly; and (b) applying one or more thrombogenic agents onto the second major surface of the polymeric substrate.

The method of the ninth aspect of the invention may have any of the preferred/optional features already set out in relation to the first aspect of the invention. In particular, the type and dimensions of the polymeric filaments, and the type and amount of thrombogenic agents may be as described with reference to the first aspect of the invention. Similarly, the polymeric substrate and the at least one polymer filament layer may have any of the dimensions, shape or physical properties described with reference to the polymeric substrate and the second polymer filament layer described in relation to the first aspect of the invention.

Step (a) may comprise forming the at least one polymer filament layer by electrospinning, as described above in relation to the seventh aspect of the invention.

The polymeric substrate may be subjected to a plasma treatment prior to step (b), as described above in relation to the seventh aspect of the invention.

The thrombogenic agents may be applied to the polymeric substrate by any suitable method, for instance, an aqueous solution of the thrombogenic agents may be applied using spray applicator, roller applicator, or by dipping a surface of the substrate into the aqueous solution.

In one preferred method, the second surface of the polymeric substrate is dipped into an aqueous solution comprising ca. 100 μg/mL of one or more thrombogenic agents to impregnate the second substrate layer with the solution of one or more thrombogenic agents. The impregnated substrate is then allowed to dry to provide a dispersion of the one or more thrombogenic agents in the second substrate layer.

The method may further comprise providing a coating of a biocompatible adhesive on the second surface of the polymeric substrate. Suitable biocompatible adhesives are as described for the first aspect of the invention.

The method may further comprise providing a physical securement means, such as a plurality of microneedles, on the second surface of the polymeric substrate.

EXAMPLES

SEM images of the patches of the invention of the patches of the invention were obtained using the following method. Sample preparation: A sample of the patch of the invention was taken and placed in a sample holder, using carbon tape to adhesively bond the sample to the holder. The sample is then placed into a gold sputtering system, the pressure reduced to 0.05 mPa and the sample sputtered with gold for 20 seconds. The chamber is then filled to ambient pressure and the sample removed. Capturing SEM image: The SEM chamber is vented to reach ambient pressure. The sample is introduced onto the sample stage and the sample compartment closed and evacuated. Electricity (up to 25 μA) is put through a tungsten filament in the SEM apparatus to heat it up. SEM images are then taken using the same conditions for all samples: spot-size=50%, voltage=10 kV, distance=10 mm, magnification=2000×.

Viscoelasticity of the patches of the invention was measured using a DMA TA-Instruments DMA Q-800. The sample (patch) was held between the clamps, and a sinusoidal stress applied to the sample. All experiments were performed at a frequency of 1 Hz, a pre-load force of 0.03 N, and an amplitude of 1.25× the pre-load force. The elastic modulus and the loss modulus were extracted by measuring the strain/stress at each time point.

Young's moduli of the patches of the invention were measured using a TA-instruments DMA Q-800. A tension assay was performed in which the sample (patch) was tensioned until a deformation produced. The instrument measured the stress each patch experienced at a particular strain. All experiments were performed with a preload force of 0.0010 N, an initial strain of 0.9%, an initial displacement of 10.0 m, and a strain ramp of 5.0% $min^{-1}$ to 30% $min^{-1}$. Young's moduli for patches of the invention are provided below.

TABLE 1

| Young's moduli for patches of the invention. | | |
|---|---|---|
| Name | Young's Modulus (MPa) | ±standard deviation/2 [MPa] |
| PCL 2000 uL/h 24.5 cm 1L-R | 1.47 | 0.177 |
| PCL 2000 uL/h 24.5 cm 1L-A | 1.52 | 0.260 |
| PCL 2000 uL/h 24.5 cm 2L-A 400 rpm | 1.18 | 0.219 |

Example 1

1.20 g of polycaprolactone (PCL) are dissolved in 10 mL of chloroform, yielding a 12% w/v concentration. The PCL pellets are added to the solvent in small portions with steady but not vigorous agitation. The mixture is ready to use once all the pellets were dissolved.

The PCL mixture is sucked by a syringe with a narrow tip to prevent bubble formation. The syringe is placed with the tip facing up, inside a fume hood to remove any existing bubbles without evaporating the solvent.

The syringe is placed on a syringe pump system and the mixture is propelled at a volumetric flow of 2000 μL/h. The syringe pump is placed horizontally, 24.5 cm away from the collector. A voltage potential of 25 kV is applied between the syringe pump and the collector. The mixture is deposited on the collector for approximately 1 hour. The patch is afterwards air dried for approximately 1 hour.

A circular patch, 15.6 mm in diameter, is cut from the total electrospun surface.

The surface of the patch is then exposed to a plasma treatment to increase the hydrophilicity of the nanofibers. A low-temperature plasma generator is used. Pure oxygen gas is ignited at a pressure of 150 Pa, and the glow discharge is ignited for 3 min. The process is carried out using an open duty cycle and a power of 70 W.

Immediately after the treatment, the patch is placed on a 24-well plate which contains 100 μL of a bioadhesive. In parallel, 200 μL of fibronectin dissolved in phosphate saline buffer (PBS) at a concentration of 100 μg/mL are placed on the superior face of the patch. After 5 min, the patch is removed from the 24-well plate.

A culture of human aortic endothelial cells, seeded at 1 million cells/cm$^2$ on a 6-well plate is injured in its center with a plastic cell scraper. The patch is placed on the injury site and pressed against the plate surface.

Cells are incubated for 48 hours in culture medium. After that, cells are fixed using 4% paraformaldehyde for 20 min at room temperature. After two consecutive washes with PBS for 10 min, cells are permeabilized with 0.2% triton (in PBS) for 10 minutes. Cells are then washed with PBS twice, ten minutes per wash, and blotted for 1 hour with 5% goat serum in PBS-BSA (PBS, 1% bovine serum albumin). Cells are labeled with phalloidin and DAPI for 1 hour. Two additional 10 min washes with PBS are performed to remove any unbound reagent.

Cells are visualized along the plate and the patch to check for migration using a fluorescence microscope. Cell density of cells migrated towards the top of the patch is quantified using the image analysis software Fiji.

Example 2

The following experiment demonstrates the effect of fiber orientation and/or the numbers of layers on cell migration within the patch of the invention.

Firstly, one-layer or two-layer PCL sheets were electrospun using the same procedure as for Example 1, with the exception that the following conditions were employed: voltage=18.6 kV, distance to the collector=18 cm, flow=2000 μL/h, volume=2 mL. Layer 1 is made using a collector with a rotating speed of 0 rpm. This layer has a random orientation of the fibers. Layer 2 is made using a collector with a rotating speed of 1000 rpm. This layer has an aligned orientation of the fibers.

Patches with 2 cm×1 cm dimensions are cut using a surgical blade. A poly(butyl acrylate: acrylic acid)-based glue (100 μL) is sprayed on each patch from a distance of 15 cm and each patch is placed on a 6-well tissue culture plate. The well is cleaned three times using 2 mL of a cell culture medium for 5 minutes. The cell culture medium used is the same used for the experiments, comprising endothelial Growth Medium-2 Complete (Promocell), with 5% Fetal Bovine Serum and 1% Penicillin/Streptomycin.

Each patch is treated with a plasma corona for 1 minute before 50 UL of bovine plasma fibronectin at 100 μg/mL is deposited onto each patch. The patches are then left for 2 hours at 37° C.

The fibronectin is then gently removed and each patch covered with a 2 cm×1 cm×1 cm silicone cap. Human aortic endothelial cells or human aortic smooth muscle cells (300,000 cells) suspended in 2.5 mL of culture medium are then seeded onto the plate and the plate left in a 5% $CO_2$, 37° C. incubator.

After 12 h, the silicone cap is removed from each patch and the medium is replaced with 2.5 mL of fresh cell culture medium. The patches are put back in the incubator, and the cell culture medium changed every 24 h. The experiment is finished 72 h after removal of the silicone cap.

The tissue culture plates are rinsed with PBS and fixed with 4% paraformaldehyde for 30 minutes at room temperature. After that, cells are cleaned twice with PBS for 5 minutes. Any excess aldehydes is quenched with a solution of glycine (0.2 mol/L) in PBS for 10 minutes and, after washing with PBS twice for 5 minutes, the cells are permeabilized with a solution of X-100 Triton (0.2%) in PBS.

After two consecutive washes with PBS for 10 minutes, the cells are labelled with phalloidin-rhodamine 1:100 and DAPI 1:1000 for 1 hour to stain the actin and nuclei of the cells.

After two consecutive 5 minutes PBS washes, the specimens were detached from the 6-well plate, placed between two microscope slides in a downwards orientation, are then imaged using a Nikon epifluorescence microscope.

Images are taken at 4× and 10× to quantify the cellular colonization of each patch, observing both the distance travelled by the cells and the cellular density, e.g. the number of cells per unit area. FIGS. 11-18 are epifluorescent images of patches of the invention.

The pixel to distance ratio is calculated using the microscope's scale embedded in the microscope's software. The cell number is quantified using the software "FIJI". Cellular invasion area density was calculated by counting the number of cells in an invaded area and dividing by the size of the area (see FIG. 17 for example). The cellular velocity is calculated as the distance travelled by the cells (see FIG. 18 for example) divided by experiment time.

Control Experiments

Control experiments were performed following the same procedure as described in Example 2, but wherein each patch is not covered with a silicone cap, allowing complete coverage of the patch with human endothelial cells/smooth muscle cells, which can adhere to each patch as if it were the 6-well tissue culture plate when they are added.

Figure 10:
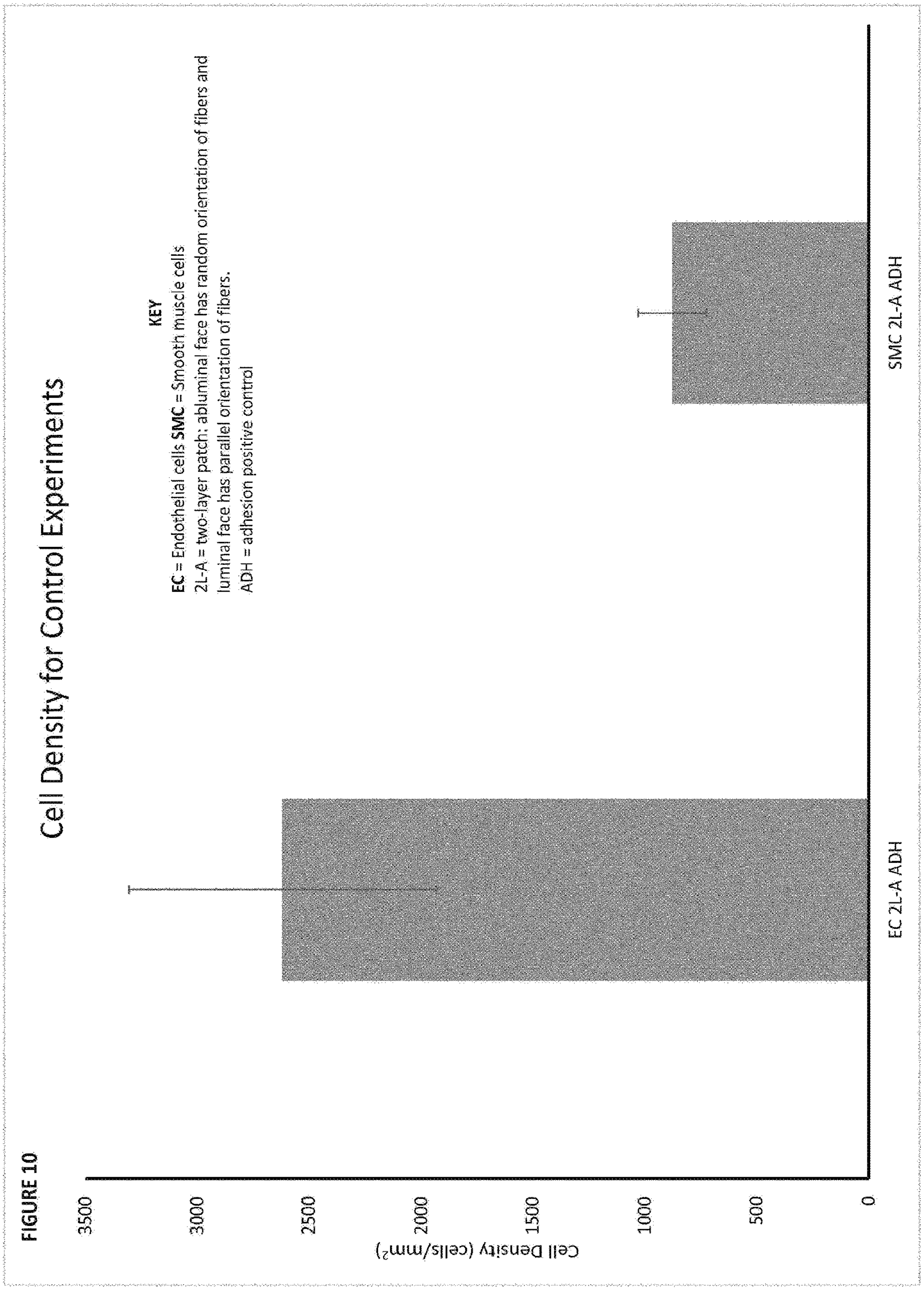
FIG. 10 is a graph showing the cell densities of human aortic endothelial cells/human smooth muscle cells for the control experiments. The data is provided in Table 2.
Figure 11:
FIG. 11 is an epifluorescence microscopy image of a patch tested according to the method of example 2, using human aortic endothelial cells. The patch is a 1-layer patch, wherein the layer has a random orientation of fibers.
Figure 12:
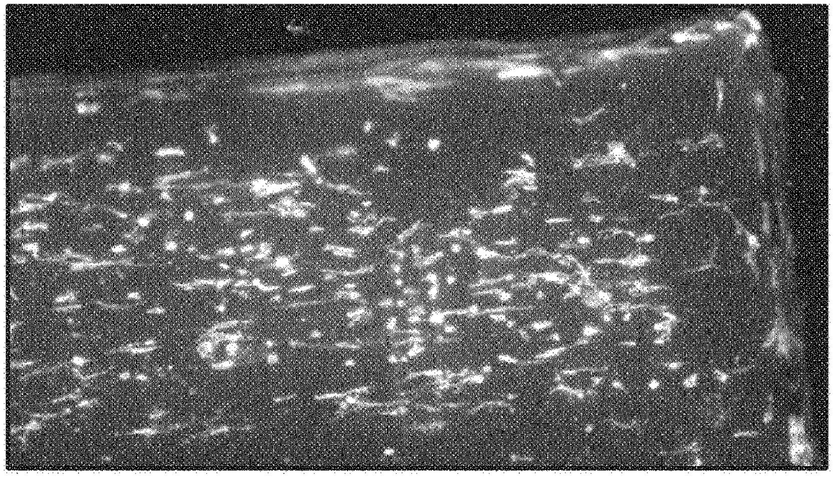
FIG. 12 is an epifluorescence microscopy image of a patch tested according to the method of example 2, using human aortic endothelial cells. The patch is a 2-layer patch, wherein both layers have a parallel orientation of fibers.
Figure 13:
FIG. 13 is an epifluorescence microscopy image of a patch tested according to the method of example 2, using human aortic endothelial cells. The patch is a 2-layer patch, wherein both layers have a random orientation of fibers.
Figure 14:
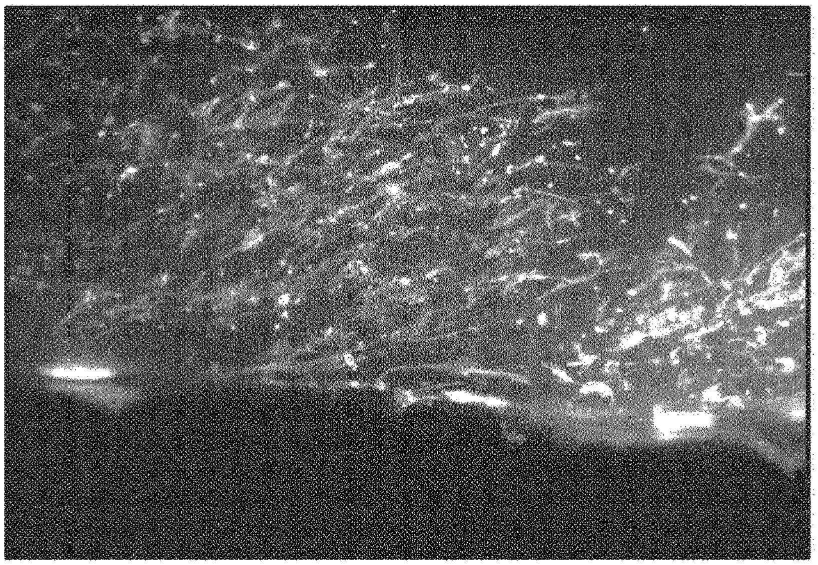
FIG. 14 is an epifluorescence microscopy image of a patch tested according to the method of example 2, using human smooth muscle cells. The patch is a 1-layer patch, wherein the layer has a random orientation of fibers.
Figure 15:
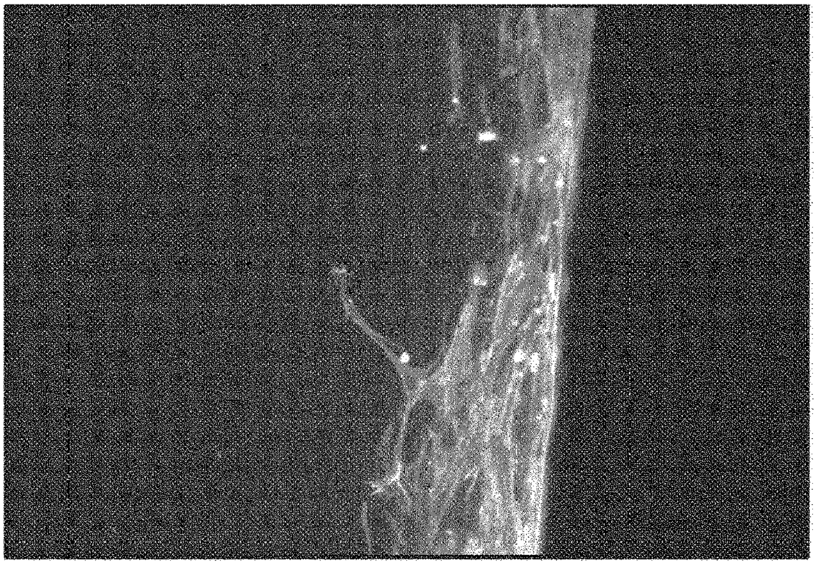
FIG. 15 is an epifluorescence microscopy image of a patch tested according to the method of example 2, using human smooth muscle cells. The patch is a 2-layer patch, wherein both layers have a parallel orientation of fibers.
Figure 16:
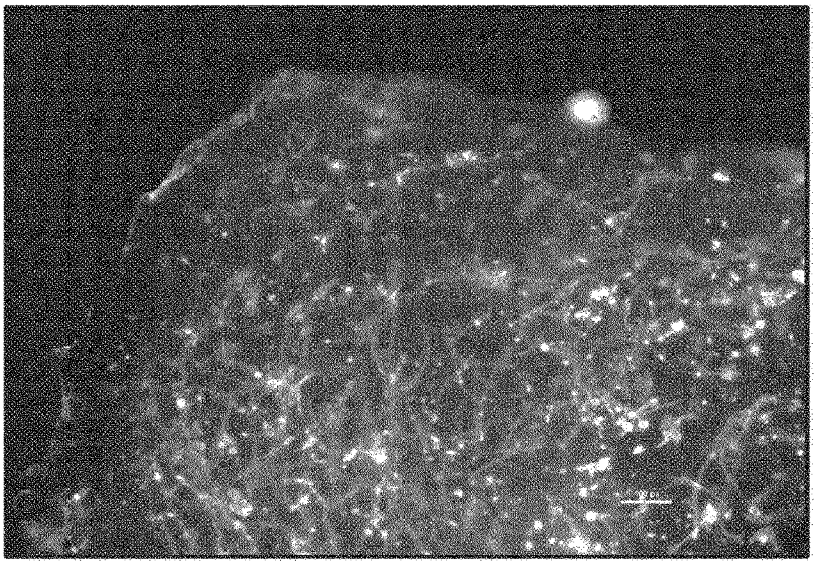
FIG. 16 is an epifluorescence microscopy image of a patch tested according to the method of example 2, using human smooth muscle cells. The patch is a 2-layer patch, wherein both layers have a random orientation of fibers.
Figure 17:
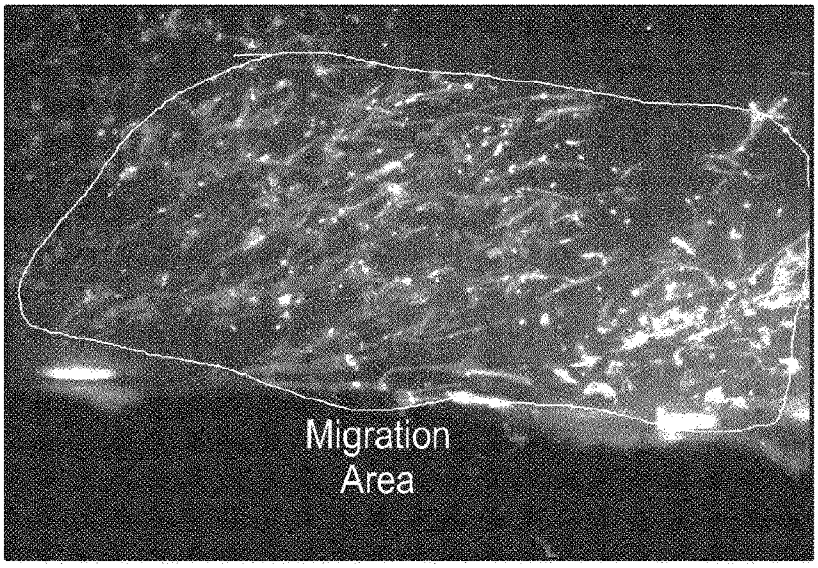
FIG. 17 is an epifluorescence microscopy image of a patch tested according to the method of example 2, depicting an example area for calculating cell density.
Figure 18:
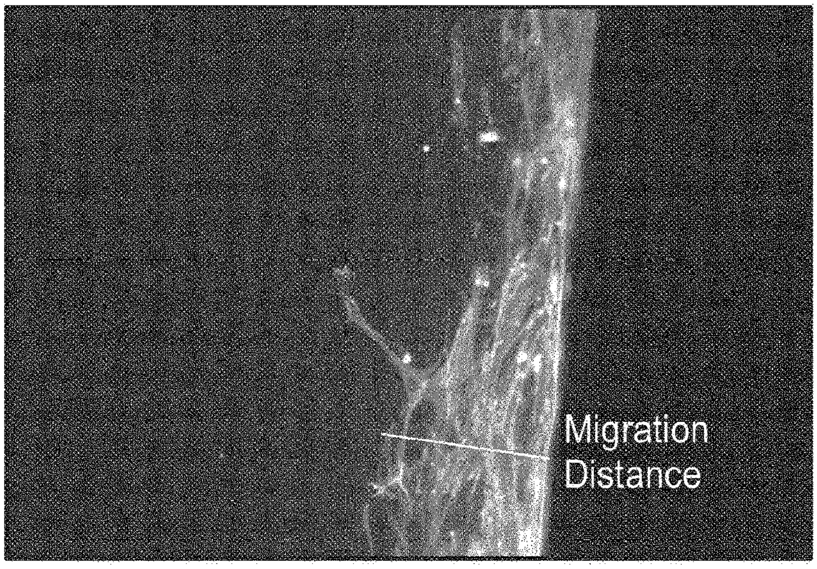
FIG. 18 is an epifluorescence microscopy image of a patch tested according to the method of example 2, depicting an example length for calculating cell velocity.
Figure 19:
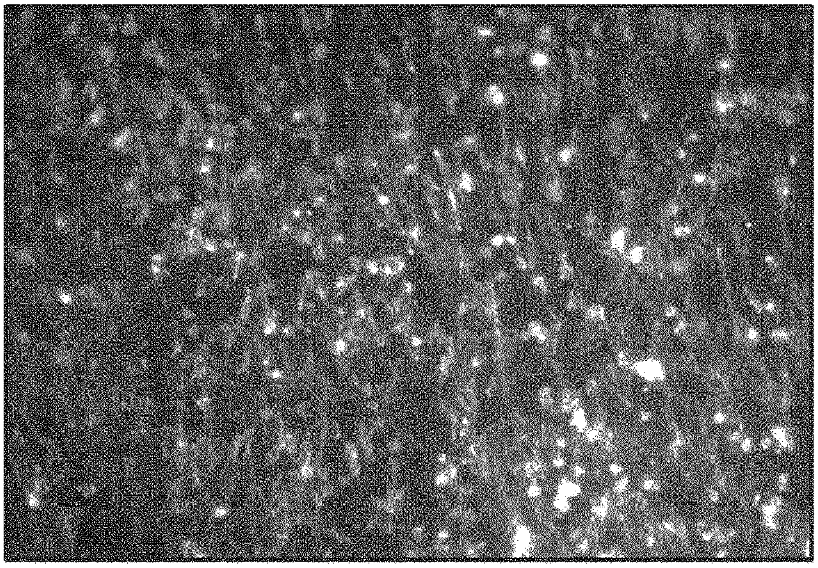
FIG. 19 is an epifluorescence microscopy image of a patch tested according to the method of the "control experiments".
Figure 20:
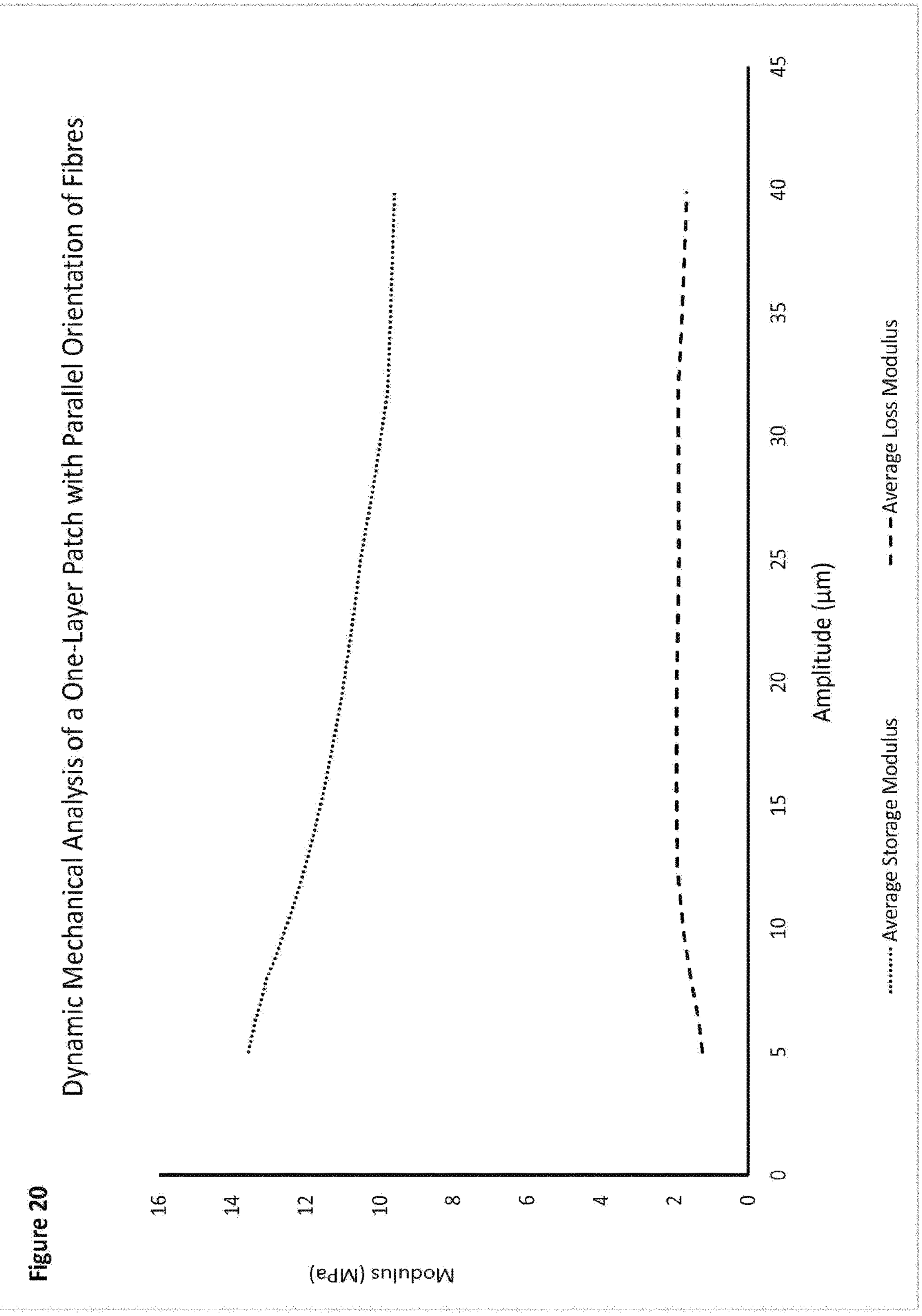
FIG. 20 is a graph showing dynamic modulus analysis (DMA) data for a one layer patch with a parallel orientation of fibers.
Figure 21:
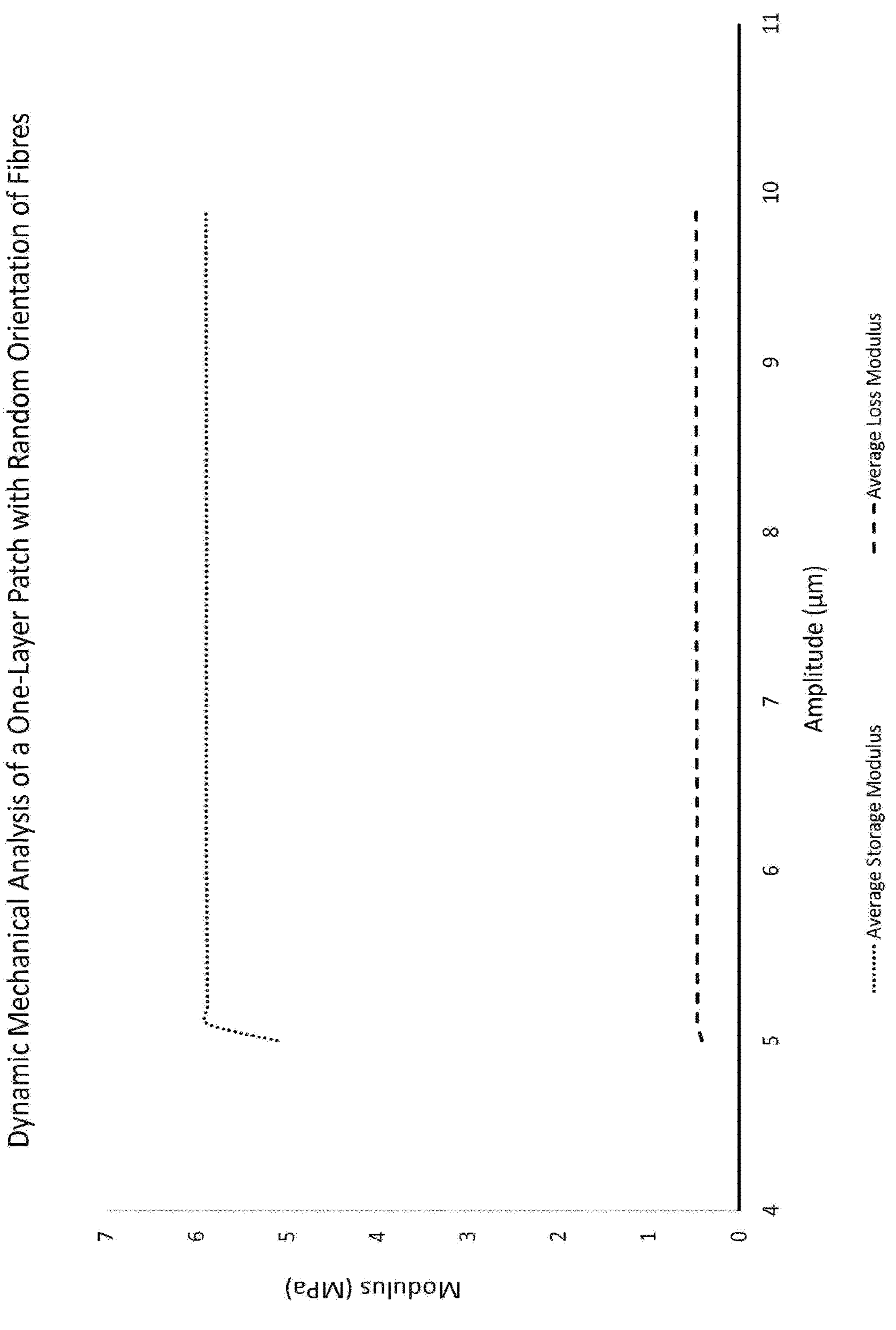
FIG. 21 is a graph showing DMA data for a one layer patch with a random orientation of fibers.
Figure 22:
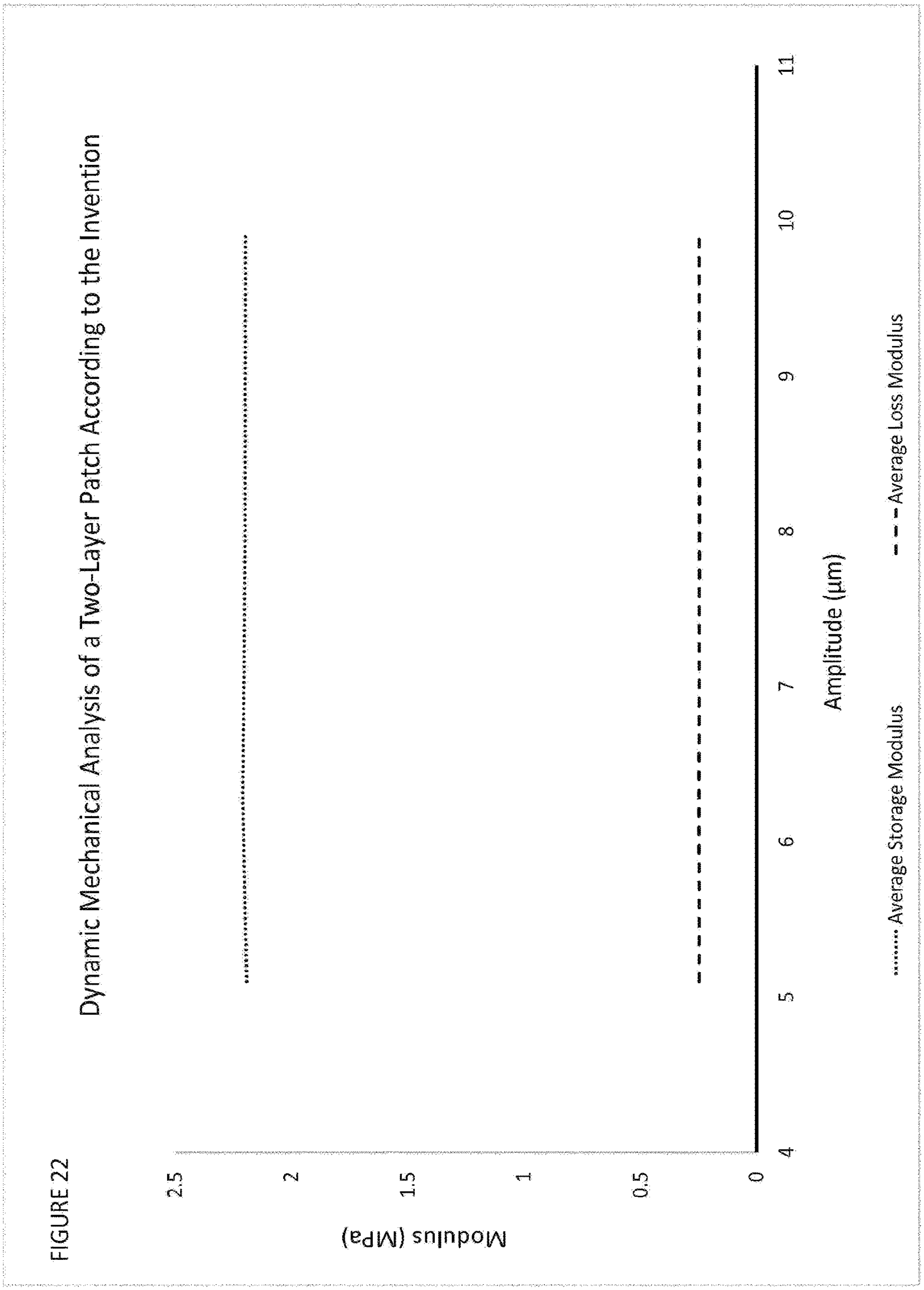
FIG. 22 is a graph showing DMA data for a patch of the invention, comprising one layer with a parallel orientation of fibers and one layer with a random orientation of fibers.

The data obtained from these experiments is therefore the control for "total" patch colonization at 72 hours. FIG. 10 displays data obtained for the control experiments for human endothelial cells and smooth muscle cells (see "ADH" entries in Table 2)

A control for colonization velocity was not measured, as the patch is "colonized" from the beginning of the experiment.

The results confirm that endothelial cells present a higher cell density when the fibers in the luminal layer are aligned than when the fibers are randomly orientated. Furthermore, endothelial cells migrate faster when the fibers within the layer are aligned than when the fibers within the layer are randomly orientated.

Smooth muscle cells present a lower cell density when the patch has two layers than when it has one. Furthermore, smooth muscle cells have a lower cell density when the fibers in the layer are aligned than when fibers in the layer are randomly orientated. Finally, smooth muscle cells migrate faster when the fibers in the layer are randomly orientated than when fibers in the layer are aligned. Aligned fibers appear to retard progression of smooth muscle cells through the patch.

TABLE 2

Average cell densities and velocities for human endothelial cells (EC) and smooth muscle cells (SMC) on the luminal face of the patch, calculated using epifluorescence microscopy. Values are averages taken from at least 7 individual samples, shown with ±standard error of the mean.

| Patch | Cells | Density (cells/mm$^2$) | Velocity (μm/h) |
|---|---|---|---|
| 1L-R | EC | 909 ± 167 | 2.4 ± 0.89 |
| 2L-R | EC | 509 ± 121 | 3.2 ± 0.74 |
| 2L-A | EC | 984 ± 327 | 6.0 ± 1.66 |
| 1L-R | SMC | 1234 ± 110 | 5.6 ± 0.70 |
| 2L-R | SMC | 631 ± 335 | 6.6 ± 1.37 |
| 2L-A | SMC | 562 ± 173 | 2.6 ± 0.80 |
| 2L-A ADH | EC | 2620 ± 687 | |
| 2L-A ADH | SMC | 876 ± 155 | |

1L-R = one-layer patch with random orientation of fibers.
1L-A = one-layer patch with parallel (aligned) orientation of fibers.
2L-R = two-layer patch: abluminal face has parallel orientation of fibers and luminal face has random orientation of fibers.
2L-A = two-layer patch: abluminal face has random orientation of fibers and luminal face has parallel orientation of fibers.
ADH = adhesion - positive control 1L-R=one-layer patch with random orientation of fibers.

1L-A=one-layer patch with parallel (aligned) orientation of fibers.

2L-R=two-layer patch: abluminal face has parallel orientation of fibers and luminal face has random orientation of fibers.

2L-A=two-layer patch: abluminal face has random orientation of fibers and luminal face has parallel orientation of fibers.

ADH=adhesion-positive control

FIGS. 8 and 9 graphically display the non-control data shown in Table 2.

The results demonstrate how the specific structural features of the patch of the present invention provide an improved patch with optimised performance in vivo. Thus, the device of the invention comprises two layers; a first layer comprising polymer filaments orientated in parallel and a second layer comprising polymer filaments orientated randomly. When in use, i.e. in vivo, the second layer is the abluminal layer (i.e. the layer in contact with smooth muscle cells), whilst the first layer is the luminal layer (i.e. the layer in contact with the blood flow). The alignment of the fibers allows endothelial cells to rapidly flow through and colonise the first (luminal) layer, facilitating faster re-endothelialization of the layer in contact with the blood flow. In addition, the random orientation of the fibers in the second (abluminal) layer allows smooth muscle cells to rapidly flow through and colonise the second layer.

The smooth muscle cells cannot however move quickly through the aligned first (luminal) layer (see FIG. 9), thus the first layer of the patch of the invention effectively provides a barrier to smooth muscle cells, such that they are predominantly present in the second (abluminal) layer.

Example 3

The inventors developed an ex-vivo test that evaluates the resistance to flow of the patch to the aorta. The test utilizes a porcine descending aorta (1.5 cm in diameter), a membrane pump actuated with pressurized air, PVC tubing, the adhesive patch of the invention, and water (at room temperature).

Firstly, a surgical punch was used to generate a 2 to 4 mm tear on the aorta. The aorta was then connected to the PVC tubing using a cable tie. The PVC tubing was connected to the membrane pump.

The membrane pump's pressurized air was stabilized at 2 barg. At this pressure, the pump delivers a pulsatile water flow at 6 L/min and 1 Hz, emulating the physiological blood flow to which the aorta is exposed.

The tear was checked to ensure that, once the pump is operative, a waterjet was observed to be emitted from the tear. If no waterjet is observed, the pump was stopped and the tear checked to ensure that it extends sufficiently through the aorta. If necessary, the tear was increased and the check repeated until a waterjet was observed being emitted from the tear.

Once the check was complete, the membrane pump was stopped and an adhesive patch according to the claims was manually introduced to cover the tear from the inside of the aorta. The patch size was 2 cm×1 cm (as in the example 2). Adhesives included ethyl cyanoacrylate (50 μL), a mixture of ethyl cyanoacrylate (100 μL) and silica particles (4%), and butyl cyanoacrylate (20 μL). Pressure was applied to the patch for 5 seconds to ensure patch adherence to the aorta. Once the patch is attached, the membrane pump is turned on again and water flows through the aorta.

With the pump running, the patch performance was evaluated visually. If the patch detaches from the aorta, the patch is ejected from the system and a water leakage from the tear is observed. If the adhesive retains the patch attached to the aorta, no water leakage is observed. It was found that the patches tested as set out above remained adhered to the aorta for the duration of the experiment and no water leakage was observed.

The invention is further described with reference to the following numbered statements.

1. A vascular repair patch comprising a polymeric substrate having first and second major surfaces, wherein the substrate comprises at least:

(i) a first polymer filament layer adjacent the first major surface comprising a plurality of polymer filaments wherein the polymer filaments are oriented in parallel; and (ii) a second polymer filament layer adjacent the second major surface comprising a plurality of polymer filaments wherein the polymer filaments are oriented randomly.

2. A vascular repair patch according to statement 1, wherein the first polymer filament layer of the vascular repair patch comprises one or more extracellular matrix compounds, optionally wherein:

(a) the one or more extracellular matrix compounds are selected from collagen (particularly collagen types I and II), elastin, fibronectin, laminins, VE-cadherin, vitronectin, integrins, heparan sulfate, chondroitin sulfate, ketaran sulfate, hyaluronic acid, and peptide sequences selected from example Arg-Gly-Asp (RGD), Arg-Glu-Asp-Val (REDV), Tyr-Ile-Gly-Ser-Arg (YIGSR); and/or (b) the first polymer filament layer comprises the one or more extracellular matrix compounds in an areal amount of from 0.5 μg/cm$^2$ to 100 μg/cm$^2$, preferably from 1 μg/cm$^2$ to 50 μg/cm$^2$, more preferably from 1.5 μg/cm$^2$ to 20 μg/cm$^2$, more preferably from 2 μg/cm$^2$ to 15 μg/cm$^2$, more preferably from 2.5 μg/cm$^2$ to 10 μg/cm$^2$, more preferably from 3 μg/cm$^2$ to 7 μg/cm$^2$, based on the surface area of the first major surface of the patch.

3. A vascular repair patch according to statement 1 or statement 2, wherein the second polymer filament layer of the polymeric substrate comprises one or more thrombogenic agents, optionally wherein:

(a) the one or more thrombogenic agents are selected from tissue factor (TF, or Factor III), Factor VII, Factor X and Fibrin; and/or (b) the second polymer filament layer comprises the one or more thrombogenic agents in an areal amount of from 0.5 g/cm$^2$ to 100 μg/cm$^2$, preferably from 1 μg/cm$^2$ to 50 μg/cm$^2$, more preferably from 1.5 μg/cm$^2$ to 20 μg/cm$^2$, more preferably from 2 μg/cm$^2$ to 15 μg/cm$^2$, more preferably from 2.5 μg/cm$^2$ to 10 μg/cm$^2$, more preferably from 3 μg/cm$^2$ to 7 μg/cm$^2$, based on the surface area of the second major surface of the patch.

4. A vascular repair patch according to any of the preceding statements, wherein the polymeric substrate is bioabsorbable, optionally wherein the polymer filaments of the first and second polymer filament layers comprise one or more bioabsorbable polymers, optionally wherein the one or more bioabsorbable polymers are selected from polylactic acid (PLA), poly-L-lactide (PLLA), poly-D-lactide (PDLA), poly-DL-lactide (PDLLA), polyglycolic acid (PGA), polyglycolide (PG), poly(lactic-co-glycolic acid) (PLGA), poly(glycolide-co-caprolactone) (PGCL), poly(glycolide-co-trimethylene carbonate (PGA-co-TMC), polycaprolactone (PCL), poly-(L-lactide-co-caprolactone) (PLLA-co-CL), poly-(D-lactide-co-caprolactone) (PDLA-co-CL), poly-(DL-lactide-co-caprolactone (PDLLA-co-CL).

5. A vascular repair patch according to statement 4, wherein the polymeric filaments of one or both of the first and second polymer filament layers comprise or consist of PCL or PGLA, wherein the PGLA has a lactide:glycolide ratio of 80:20 to 20:80, optionally wherein the polymeric filaments of at least one of the first and second polymer filament layers comprise at least 50 wt % PCL, preferably at least 60 wt % PCL, more preferably at least 70 wt % PCL, more preferably at least 80 wt % PCL.

6. A vascular repair patch according to statement 5, wherein the polymeric filaments of at least one of the first and second polymer filament layers comprise at least 50 wt % PCL and up to 50 wt % of PLA, PLLA, PDLA, PDLLA, PGA, PG, PLGA, PGCL, PLLA-CO-CL, PDLA-co-CL, or PDLLA-co-CL, optionally wherein the polymeric filaments of at least one of the first and second polymer filament layers comprise at least 50 wt % PCL and up to 50 wt % of PLGA, preferably at least 60 wt % PCL and up to 40 wt % of PLGA, more preferably at least 70 wt % PCL and up to 30 wt % of PLGA, more preferably at least 80 wt % PCL and up to 20 wt % of PLGA.

7. A vascular repair patch according to any of the preceding statements, wherein:

(a) the polymeric filaments of the first and second polymer filament layers have an average filament diameter in the range of from 1 to 20 μm, more preferably from 1 to 15 μm, more preferably from 2 to 10 μm, more preferably from 3 to 8 μm, more preferably about 5 μm; and/or (b) the filament diameters of at least one of the first and second polymer filament layers form a bimodal distribution with one peak in the range of from 0.2 to 2 μm and a second peak in the range of from 2.5 to 10 μm; and/or (c) the polymeric filaments of the first and second polymer filament layers are electrospun filaments; and/or (d) the filaments of the first polymer filament layer are oriented with a standard deviation of no more than 36°, preferably no more than 18°; and/or (e) the filaments of the second polymer filament layer are oriented with a standard deviation of at least 45°, preferably at least 54°, more preferably at least 63°, more preferably at least 72°, more preferably at least 81°, more preferably at least 90°.

8. A vascular repair patch according to any of the preceding statements, wherein the polymeric substrate has a Young's modulus in the range of from 0.5 to 3.0 MPa.

9. A vascular repair patch according to any of the preceding statements, wherein the second polymer filament layer has an average porosity of from 30 to 70%, preferably from 40 to 60%, more preferably around 50% and/or an average pore diameter in the range of from 50 to 300 μm, more preferably from 100 to 250 μm, more preferably from 150 to 200 μm.

10. A vascular repair patch according to any of the preceding statements, wherein each of the first and second polymer filament layers independently has a thickness in the range of from 10 μm to 200 μm, more preferably from 20 μm to 100 μm, more preferably from 30 μm to 70 μm, for example about 50 μm.

11. A vascular repair patch according to any of the preceding statements, having:

(a) a total thickness in the range of 20 μm to 500 μm, more preferably from 50 μm to 200 μm, more preferably from 50 μm to 150 μm, for example about 100 μm; and/or (b) a length and a width independently in the range of from 10 to 50 mm, more preferably from 20 to 40 mm.

12. A vascular repair patch according to any of the preceding statements, wherein the filaments of the first polymer filament layer lie substantially parallel to the length direction of the vascular repair patch and the length of the patch is greater than the width, preferably wherein the length of the patch is at least 20% or at least 50% greater than the width.

13. A vascular repair patch according to any of the preceding statements, wherein a coating of a biocompatible adhesive is disposed on the second major surface of the polymeric substrate, optionally wherein the biocompatible adhesive is selected from synthetic adhesives (such as acrylates, cyanoacrylates and polyurethanes) and natural polymers (such as hyaluronic acids, celluloses and alginates).
14. A vascular repair patch according to any of the preceding statements, wherein the second surface of the polymeric substrate comprises a physical securement means adapted to secure the vascular repair patch to a vascular wall, optionally wherein the physical securement means comprises a plurality of microneedles, optionally wherein the plurality of microneedles are formed of a bioabsorbable material.
15. A method of making a vascular repair patch as defined in any of statements 1 to 14, the method comprising:
(a) providing a polymeric substrate having first and second major surfaces by forming at least one of (i) a first polymer filament layer comprising a plurality of polymer filaments wherein the polymer filaments are oriented in parallel; and (ii) a second polymer filament layer comprising a plurality of polymer filaments wherein the polymer filaments are oriented randomly; and optionally further comprising the steps of:
(b) applying one or more extracellular matrix compounds onto the first major surface of the polymeric substrate; and/or
(c) applying one or more thrombogenic agents onto the second major surface of the polymeric substrate.
16. A vascular repair patch comprising a polymeric substrate having first and second major surfaces, wherein the substrate comprises at least:
(i) a first polymer filament layer adjacent the first major surface comprising a plurality of polymer filaments wherein the polymer filaments are oriented in parallel; and
(ii) a second polymer filament layer adjacent the second major surface comprising a plurality of polymer filaments wherein the polymer filaments are oriented randomly.
17. A vascular repair patch according to statement 16, wherein the polymeric substrate is bioabsorbable.
18. A vascular repair patch according to statement 17, wherein the polymer filaments of the first and second polymer filament layers comprise one or more bioabsorbable polymers.
19. A vascular repair patch according to statement 18, wherein the one or more bioabsorbable polymers are selected from polylactic acid (PLA), poly-L-lactide (PLLA), poly-D-lactide (PDLA), poly-DL-lactide (PDLLA), polyglycolic acid (PGA), polyglycolide (PG), poly(lactic-co-glycolic acid) (PLGA), poly(glycolide-co-caprolactone) (PGCL), poly(glycolide-co-trimethylene carbonate (PGA-co-TMC), polycaprolactone (PCL), poly-(L-lactide-co-caprolactone) (PLLA-co-CL), poly-(D-lactide-co-caprolactone) (PDLA-co-CL), poly-(DL-lactide-co-caprolactone (PDLLA-co-CL).
20. A vascular repair patch according to statement 19, wherein the polymeric filaments of at least one of the first and second polymer filament layers comprise or consist of PCL or PGLA, wherein the PGLA has a lactide:glycolide ratio of 80:20 to 20:80.
21. A vascular repair patch according to statement 20, wherein the polymeric filaments of both the first and second polymer filament layers comprise or consist of PCL or PGLA, wherein the PGLA has a lactide:glycolide ratio of 80:20 to 20:80.
22. A vascular repair patch according to statement 20 or statement 21, wherein the polymeric filaments of at least one of the first and second polymer filament layers comprise at least 50 wt % PCL, preferably at least 60 wt % PCL, more preferably at least 70 wt % PCL, more preferably at least 80 wt % PCL. For instance, the polymeric filaments of at least one of the first and second polymer filament layers may comprise at least 90 wt % PCL, at least 95 wt % PCL, at least 98 wt % PCL, at least 99 wt % PCL, or 100 wt % PCL.
23. A vascular repair patch according to statement 22, wherein the polymeric filaments of at least one of the first and second polymer filament layers comprise at least 50 wt % PCL and up to 50 wt % of PLA, PLLA, PDLA, PDLLA, PGA, PG, PLGA, PGCL, PLLA-co-CL, PDLA-co-CL, or PDLLA-co-CL.
24. A vascular repair patch according to statement 23, wherein the polymeric filaments of at least one of the first and second polymer filament layers comprise at least 50 wt % PCL and up to 50 wt % of PLGA, preferably at least 60 wt % PCL and up to 40 wt % of PLGA, more preferably at least 70 wt % PCL and up to 30 wt % of PLGA, more preferably at least 80 wt % PCL and up to 20 wt % of PLGA.
25. A vascular repair patch according to any one of statements 16 to 24, wherein the polymeric filaments of the first and second polymer filament layers have an average filament diameter in the range of from 1 to 20 μm, more preferably from 1 to 15 μm, more preferably from 2 to 10 μm, more preferably from 3 to 8 μm, more preferably about 5 μm.
26. A vascular repair patch according to any one of statements 16 to 25, wherein the filament diameters of at least one of the first and second polymer filament layers form a bimodal distribution with one peak in the range of from 0.2 to 2 μm and a second peak in the range of from 2.5 to 10 μm.
27. A vascular repair patch according to any one of statements 16 to 26, wherein the polymeric filaments of the first and second polymer filament layers are electrospun filaments.
28. A vascular repair patch according to any one of statements 16 to 27, wherein the polymeric substrate has a Young's modulus in the range of from 0.5 to 3.0 MPa.
29. A vascular repair patch according to any one of statements 16 to 28, wherein the filaments of the first polymer filament layer are oriented with a standard deviation of no more than 36°, preferably no more than 18°.
30. A vascular repair patch according to any one of statements 16 to 29, wherein the filaments of the second polymer filament layer are oriented with a standard deviation of at least 45°, preferably at least 54°, more preferably at least 63°, more preferably at least 72°, more preferably at least 81°, more preferably at least 90°.
31. A vascular repair patch according to statement 30, wherein the filaments of the first polymer filament layer are oriented with a standard deviation of no more than 36° and the filaments of the second polymer filament layer are oriented with a standard deviation of at least 45°, preferably at least 54°, more preferably at least 63°, more preferably at least 72°.

32. A vascular repair patch according to statement 31, wherein the filaments of the first polymer filament layer are oriented with a standard deviation of no more than 18° and the filaments of the second polymer filament layer are oriented with a standard deviation of at least 63°, more preferably at least 72°, more preferably at least 81°, more preferably at least 90°.
33. A vascular repair patch according to any one of statements 16 to 32, wherein the second polymer filament layer has an average porosity of from 30 to 70%, preferably from 40 to 60%, more preferably around 50%.
34. A vascular repair patch according to any one of statements 16 to 33, wherein the second polymer filament layer suitably has an average pore diameter in the range of from 50 to 300 μm, more preferably from 100 to 250 μm, more preferably from 150 to 200 μm.
35. A vascular repair patch according to any one of statements 16 to 34, wherein each of the first and second polymer filament layers independently has a thickness in the range of from 10 μm to 200 μm, more preferably from 20 μm to 100 μm, more preferably from 30 μm to 70 μm, for example about 50 μm.
36. A vascular repair patch according to any one of statements 16 to 35, having a total thickness in the range of 20 μm to 500 μm, more preferably from 50 μm to 200 μm, more preferably from 50 μm to 150 μm, for example about 100 μm.
37. A vascular repair patch according to any one of statements 16 to 36, having a length and a width independently in the range of from 10 to 50 mm, more preferably from 20 to 40 mm.
38. A vascular repair patch according to statement 37, having a length of from 25 to 35 mm and a width of from 15 to 25 mm, more preferably a length of 30 mm and a width of 20 mm.
39. A vascular repair patch according to any one of statements 16 to 38, wherein the filaments of the first polymer filament layer lie substantially parallel to the length direction of the vascular repair patch and the length of the patch is greater than the width, preferably wherein the length of the patch is at least 20% or at least 50% greater than the width.
40. A vascular repair patch according to any one of statements 16 to 39, wherein the first polymer filament layer of the vascular repair patch comprises one or more extracellular matrix compounds.
41. A vascular repair patch according to any one of statements 16 to 40, wherein the one or more extracellular matrix compounds are selected from collagen (particularly collagen types I and II), elastin, fibronectin, laminins, VE-cadherin, vitronectin, integrins, heparan sulfate, chondroitin sulfate, ketaran sulfate, hyaluronic acid, and peptide sequences selected from example Arg-Gly-Asp (RGD), Arg-Glu-Asp-Val (REDV), Tyr-Ile-Gly-Ser-Arg (YIGSR).
42. A vascular repair patch according to statement 40 or statement 41, wherein the first polymer filament layer comprises the one or more extracellular matrix compounds in an areal amount of from 0.5 μg/cm$^2$ to 100 μg/cm$^2$, preferably from 1 μg/cm$^2$ to 50 μg/cm$^2$, more preferably from 1.5 μg/cm$^2$ to 20 μg/cm$^2$, more preferably from 2 μg/cm$^2$ to 15 μg/cm$^2$, more preferably from 2.5 μg/cm$^2$ to 10 μg/cm$^2$, more preferably from 3 μg/cm$^2$ to 7 μg/cm$^2$, based on the surface area of the first major surface of the patch.
43. A vascular repair patch according to any one of statements 15 to 42, wherein a coating of a biocompatible adhesive is disposed on the second major surface of the polymeric substrate.
44. A vascular repair patch according to statement 43, wherein the biocompatible adhesive is selected from synthetic adhesives (such as acrylates, cyanoacrylates and polyurethanes) and natural polymers (such as hyaluronic acids, celluloses and alginates).
45. A vascular repair patch according to any one of statements 16 to 44, wherein the second surface of the polymeric substrate comprises a physical securement means adapted to secure the vascular repair patch to a vascular wall, optionally wherein the physical securement means comprises a plurality of microneedles, optionally wherein the plurality of microneedles are formed of a bioabsorbable material.

46. A vascular repair patch according to any one of statements 16 to 45, wherein the second polymer filament layer of the polymeric substrate comprises one or more thrombogenic agents.
47. A vascular repair patch according to statement 46, wherein the one or more thrombogenic agents are selected from tissue factor (TF, or Factor III), Factor VII, Factor X and Fibrin.
48. A vascular repair patch according to statement 46 or statement 47, wherein the second polymer filament layer comprises the one or more thrombogenic agents in an areal amount of from 0.5 μg/cm$^2$ to 100 μg/cm$^2$, preferably from 1 μg/cm$^2$ to 50 μg/cm$^2$, more preferably from 1.5 μg/cm$^2$ to 20 μg/cm$^2$, more preferably from 2 μg/cm$^2$ to 15 μg/cm$^2$, more preferably from 2.5 μg/cm$^2$ to 10 μg/cm$^2$, more preferably from 3 μg/cm$^2$ to 7 μg/cm$^2$, based on the surface area of the second major surface of the patch.
49. A vascular repair patch comprising a polymeric substrate having first and second major surfaces, wherein the polymeric substrate comprises at least one polymer filament layer adjacent the first major surface; and wherein one or more extracellular matrix-compounds are disposed on the first major surface of the polymeric substrate.
50. A vascular repair patch according to statement 49, wherein the one or more extracellular matrix compounds are selected from collagen (particularly collagen types I and II), elastin, fibronectin, laminins, VE-cadherin, vitronectin, integrins, heparan sulfate, chondroitin sulfate, ketaran sulfate, hyaluronic acid, and peptide sequences selected from example Arg-Gly-Asp (RGD), Arg-Glu-Asp-Val (REDV), Tyr-Ile-Gly-Ser-Arg (YIGSR).
51. A vascular repair patch according to statement 49 or statement 50, wherein the at least one polymer filament layer comprises the one or more extracellular matrix compounds in an areal amount of from 0.5 μg/cm$^2$ to 100 g/cm$^2$, preferably from 1 μg/cm$^2$ to 50 g/cm$^2$, more preferably from 1.5 μg/cm$^2$ to 20 μg/cm$^2$, more preferably from 2 μg/cm$^2$ to 15 μg/cm$^2$, more preferably from 2.5 μg/cm$^2$ to 10 μg/cm$^2$, more preferably from 3 μg/cm$^2$ to 7 μg/cm$^2$, based on the surface area of the first major surface of the patch.
52. A vascular repair patch according to any of statements 49 to 51, wherein the at least one polymer filament layer preferably comprises a plurality of polymer filaments, wherein the polymer filaments are oriented in parallel.

53. A vascular repair patch according to any of statements 49 to 52, wherein the polymeric substrate is bioabsorbable.
54. A vascular repair patch according to statement 53, wherein the polymer filaments of the at least one polymer filament layer comprises one or more bioabsorbable polymers.
55. A vascular repair patch according to statement 54, wherein the polymer filaments are as defined in any one of claims 4 to 12.
56. A vascular repair patch according to any one of statements 49 to 55, wherein the second surface of the vascular repair patch is provided with a coating of a biocompatible adhesive, preferably wherein the biocompatible adhesive is selected from synthetic adhesives (such as acrylates, cyanoacrylates and polyurethanes) and natural polymers (such as hyaluronic acids, celluloses and alginates).
57. A vascular repair patch according to one of statements 49 to 56, wherein the second surface of the polymeric substrate comprises a physical securement means adapted to secure the vascular repair patch to a vascular wall, optionally wherein the physical securement means comprises a plurality of microneedles, optionally wherein the plurality of microneedles are formed of a bioabsorbable material.
58. A vascular repair patch comprising a polymeric substrate having first and second major surfaces, wherein the polymeric substrate comprises at least one polymer filament layer adjacent the second major surface; and wherein one or more thrombogenic agents are disposed on the second major surface of the polymeric substrate.
59. A vascular repair patch according to statement 58, wherein the one or more thrombogenic agents are selected from one or more components of the coagulation cascade, for example tissue factor (TF, or Factor III), Factor VII, Factor X and Fibrin.
60. A vascular repair patch according to statement 58 or statement 59, wherein the at least one polymer filament layer comprises the one or more thrombogenic agents in an areal amount of from 0.5 $\mu g/cm^2$ to 100 $\mu g/cm^2$, preferably from 1 $\mu g/cm^2$ to 50 $\mu g/cm^2$, more preferably from 1.5 $\mu g/cm^2$ to 20 $\mu g/cm^2$, more preferably from 2 $\mu g/cm^2$ to 15 $\mu g/cm^2$, more preferably from 2.5 $\mu g/cm^2$ to 10 $\mu g/cm^2$, more preferably from 3 $\mu g/cm^2$ to 7 $\mu g/cm^2$, based on the surface area of the second major surface of the patch.
61. A vascular repair patch according to any of statements 58 to 60, wherein the at least one polymer filament layer preferably comprises a plurality of polymer filaments, wherein the polymer filaments are randomly oriented.
62. A vascular repair patch according to according to any of statements 58 to 61, wherein the polymeric substrate is bioabsorbable.
63. A vascular repair patch according to statement 62, wherein the polymer filaments of the at least one polymer filament layer comprises one or more bioabsorbable polymers.
64. A vascular repair patch according to statement 63, wherein the polymer filaments are as defined in any one of claims 4 to 12.
65. A vascular repair patch according to any one of statements 58 to 64, wherein the second surface of the vascular repair patch is provided with a coating of a biocompatible adhesive, preferably wherein the biocompatible adhesive is selected from synthetic adhesives (such as acrylates, cyanoacrylates and polyurethanes) and natural polymers (such as hyaluronic acids, celluloses and alginates).
66. A vascular repair patch according to one of statements 58 to 65, wherein the second surface of the polymeric substrate comprises a physical securement means adapted to secure the vascular repair patch to a vascular wall, optionally wherein the physical securement means comprises a plurality of microneedles, optionally wherein the plurality of microneedles are formed of a bioabsorbable material.
67. A method of treating a vascular defect, the method comprising positioning a vascular repair patch as defined in any one of statements 16 to 66 across the vascular defect such that the vascular repair patch conforms to the inside of the vascular wall.
68. A method according to statement 67, wherein the vascular defect is a tear in a vascular wall, preferably wherein the vascular defect is an aortic dissection.
69. A method according to statement 67 or statement 68, wherein the vascular repair patch is deployed by an endovascular delivery system, e.g. using a catheter or guide wire to deploy the vascular repair patch.
70. A method according to any one of statements 67 to 69, wherein the vascular repair patch is deployed such that the first surface forms the luminal side of the patch and the second surface forms the abluminal side of the patch.
71. An extracellular matrix compound for use in a method of treating a vascular defect, wherein the extracellular matrix compound is in the form of a vascular repair patch as defined in any of statements 40 to 42 and 49 to 57, wherein the method comprises positioning the vascular repair patch across the vascular defect such that the vascular repair patch conforms to the inside of the vascular wall.
72. An thrombogenic agent for use in a method of treating a vascular defect, wherein the thrombogenic agent is in the form of a vascular repair patch as defined in any of statements 46 to 48 and 58 to 66, wherein the method comprises positioning the vascular repair patch across the vascular defect such that the vascular repair patch conforms to the inside of the vascular wall.
73. A method of making a vascular repair patch as defined in any one of statements 16 to 48, the method comprising:
(a) providing a polymeric substrate having first and second major surfaces by forming at least one of (i) a first polymer filament layer comprising a plurality of polymer filaments wherein the polymer filaments are oriented in parallel; and (ii) a second polymer filament layer comprising a plurality of polymer filaments wherein the polymer filaments are oriented randomly.
74. A method according to statement 73, further comprising the steps of:
(b) applying one or more extracellular matrix compounds onto the first major surface of the polymeric substrate; and/or
(c) applying one or more thrombogenic agents onto the second major surface of the polymeric substrate.
75. A method of making a vascular repair patch as defined in any one of statements 49 to 57, the method comprising:
(a) providing a polymeric substrate having first and second major surfaces by forming at least one polymer filament layer comprising a plurality of polymer filaments wherein the polymer filaments are oriented in parallel; and (b) applying one or more extracellular matrix compounds onto the first major surface of the polymeric substrate.

76. A method of making a vascular repair patch as defined in any one of statements 58 to 66, the method comprising:

(a) providing a polymeric substrate having first and second major surfaces by forming at least one polymer filament layer comprising a plurality of polymer filaments wherein the polymer filaments are oriented randomly; and (b) applying one or more thrombogenic agents onto the second major surface of the polymeric substrate.

77. A method of treating a vascular defect, the method comprising positioning a thrombogenic agent in the form of a vascular repair patch as defined in any of statements 46 to 48 and 58 to 66 across the vascular defect such that the vascular repair patch conforms to the inside of the vascular wall.

The foregoing is a detailed description of the invention to aid those skilled in the art to practice the invention as defined in the claims. Various modifications and variations may be made to the specific embodiments of the invention described herein without departing from the spirit and scope of the invention. Unless specified otherwise, all technical and scientific terms used herein have the same meaning as is commonly understood by those skilled in the art to which this invention belongs. All publications, patent applications, patents and other references identified herein are incorporated by reference in their entirety.

What is claimed is:

1. A vascular repair patch comprising a polymeric substrate having first and second major surfaces, wherein the substrate comprises at least:

(i) a first polymer filament layer adjacent the first major surface comprising a plurality of polymer filaments wherein the polymer filaments are oriented in parallel; and (ii) a second polymer filament layer adjacent the second major surface comprising a plurality of polymer filaments wherein the polymer filaments are oriented randomly; wherein:

the polymer filaments of the first and second polymer filament layers comprise at least 50 wt % polycaprolactone (PCL);

the polymer filaments of the first and second polymer filament layers have an average filament diameter in a range of from 1 to 20 μm, and the diameters of the polymer filaments of at least one of the first and second polymer filament layers form a bimodal distribution with one peak in a range of from 0.2 to 2 μm and a second peak in a range of from 2.5 to 10 μm;

the polymeric substrate has a Young's modulus in a range of from 0.5 to 3.0 MPa;

the polymer filaments of the first polymer filament layer are oriented with a standard deviation of no more than 18°, and the polymer filaments of the second polymer filament layer are oriented with a standard deviation of at least 63°;

the second polymer filament layer has an average porosity of from 40 to 60%;

the vascular repair patch has a total thickness in a range of from 50 μm to 500 μm, and second polymer filament layers independently has a thickness in a range of from 20 μm to 200 μm.

2. The vascular repair patch of claim 1, wherein the polymer filaments of the first and second polymer filament layers further comprise up to 50 wt % poly(lactic-co-glycolic acid) (PLGA), wherein the PLGA has a lactide: glycolide ratio of 80:20 to 20:80.

3. The vascular repair patch of 2, wherein the first major surface is a luminal surface of the polymeric substrate and the second major surface is an abluminal surface of the polymeric substrate, wherein the abluminal surface is configured for securement to the inner vascular wall.

4. The vascular repair patch of claim 3, wherein the abluminal surface comprises a securement adapted to secure the abluminal surface to the inner vascular wall and the securement is a physical securement or a biocompatible adhesive.

5. The vascular repair patch according to claim 4, wherein the physical securement is a plurality of microneedles.

6. The vascular repair patch according to claim 1, wherein the first polymer filament layer forms the bimodal distribution such that the first polymer filament layer has first polymer filaments with an average diameter of the one peak in the range of from 0.2 to 2 μm and has second polymer filaments with an average diameter of the second peak in the range of from 2.5 to 10 μm.

7. The vascular repair patch according to claim 6, wherein the second polymer filament layer forms the bimodal distribution such that the second polymer filament layer has first polymer filaments with an average diameter of the one peak in the range of from 0.2 to 2 μm and second polymer filaments with an average diameter of the second peak in the range of from 2.5 to 10 μm.

8. The vascular repair patch according to claim 7, wherein the first polymer filament layer and the second polymer filament layer form the bimodal distribution such that the first polymer filament layer has first polymer filaments with an average diameter of the one peak in the range of from 0.2 to 2 μm and has second polymer filaments with an average diameter of the second peak in the range of from 2.5 to 10 μm.

9. The vascular repair patch of claim 1, wherein the first polymer filament layer and the second polymer filament layer form the bimodal distribution.

10. The vascular repair patch according to claim 9, wherein the first polymer filament layer has polymer filaments with an average diameter of the one peak in the range of from 0.2 to 2 μm and the second polymer filament layer has polymer filaments of the second peak in the range of from 2.5 to 10 μm.

11. The vascular repair patch according to claim 10, wherein the polymer filaments of at least one of the first and second polymer filament layers comprise polycaprolactone (PCL) and a second bioabsorbable polymer selected from the group consisting of polylactic acid (PLA), poly-L-lactic acid (PLLA), poly-D-lactic acid (PDLA), poly-DL-lactic acid (PDLLA), polyglycolic acid (PGA), polyglycolide (PG), poly(lactic-co-glycolic acid) (PLGA), poly(glycolide-co-caprolactone) (PGCL), poly(L-lactide-co-caprolactone) (PLLA-co-CL), poly(D-lactide-co-caprolactone) (PDLA-co-CL), and poly(DL-lactide-co-caprolactone) (PDLLA-co-CL).

12. The vascular repair patch according to claim 11, wherein the polycaprolactone (PCL) is present in the polymer filaments in amount of at least 50 wt % polycaprolactone (PCL) and the second bioabsorbable polymer is present in an amount up to 50 wt %.

13. The vascular repair patch according to claim 12, wherein the second bioabsorbable polymer is poly(lactic-co-glycolic acid) (PLGA).

14. The vascular repair patch according to claim 13, wherein the first polymer filament layer of the vascular repair patch comprises one or more extracellular matrix compounds in an areal amount of from 1 $\mu g/cm^2$ to 50 $\mu g/cm^2$, based on a surface area of the first major surface of the vascular repair patch, and wherein the one or more extracellular matrix compounds are selected from collagen (particularly collagen types I and II), elastin, fibronectin, laminins, VE-cadherin, vitronectin, integrins, heparan sulfate, chondroitin sulfate, ketaran sulfate, hyaluronic acid, and peptide sequences selected from Arg-Gly-Asp (RGD), Arg-Glu-Asp-Val (REDV), or Tyr-Ile-Gly-Ser-Arg (YIGSR).

15. The vascular repair patch according to claim 14, wherein the second polymer filament layer comprises one or more thrombogenic agents in an areal amount of from 0.5 $\mu g/cm^2$ to 100 $\mu g/cm^2$, based on a surface area of the second major surface of the patch, and wherein the one or more thrombogenic agents are selected from tissue factor (TF, or Factor III), Factor VII, Factor X and Fibrin.

16. The vascular repair patch according to claim 1, wherein the polymer filaments of at least one of the first and second polymer filament layers comprise polycaprolactone (PCL) and a second bioabsorbable polymer selected from the group consisting of polylactic acid (PLA), poly-L-lactic acid (PLLA), poly-D-lactic acid (PDLA), poly-DL-lactic acid (PDLLA), polyglycolic acid (PGA), polyglycolide (PG), poly(lactic-co-glycolic acid) (PLGA), poly(glycolide-co-caprolactone) (PGCL), poly(L-lactide-co-caprolactone) (PLLA-co-CL), poly(D-lactide-co-caprolactone) (PDLA-co-CL), and poly(DL-lactide-co-caprolactone) (PDLLA-co-CL).

17. The vascular repair patch according to claim 16, wherein the polycaprolactone (PCL) is present in the polymer filaments in amount of at least 50 wt % polycaprolactone (PCL) and the second bioabsorbable polymer is present in an amount up to 50 wt %.

18. The vascular repair patch according to claim 17, wherein the second bioabsorbable polymer is poly(lactic-co-glycolic acid) (PLGA).

* * * * *